US009782214B2

United States Patent
Houser et al.

(10) Patent No.: US 9,782,214 B2
(45) Date of Patent: Oct. 10, 2017

(54) SURGICAL INSTRUMENT WITH SENSOR AND POWERED CONTROL

(75) Inventors: Kevin L. Houser, Springboro, OH (US); Foster B. Stulen, Mason, OH (US); William D. Dannaher, Cincinnati, OH (US); Frederick E. Shelton, IV, Hillsboro, OH (US); Geoffrey S. Strobl, Williamsburg, OH (US); Aaron C. Voegele, Loveland, OH (US); Timothy P. Lessek, Mason, OH (US); Gavin M. Monson, Oxford, OH (US); Barry C. Worrell, Centerville, OH (US); Hitesh Jain, Rajasthan (IN)

(73) Assignee: Ethicon LLC, Guaynabo, PR (US)

( * ) Notice: Subject to any disclaimer, the term of this patent is extended or adjusted under 35 U.S.C. 154(b) by 1280 days.

(21) Appl. No.: 13/277,328

(22) Filed: Oct. 20, 2011

(65) Prior Publication Data

US 2012/0116391 A1     May 10, 2012

Related U.S. Application Data

(63) Continuation-in-part of application No. 13/151,481, filed on Jun. 2, 2011.
(Continued)

(51) Int. Cl.
    *A61B 18/14*        (2006.01)
    *A61B 17/32*        (2006.01)
(Continued)

(52) U.S. Cl.
    CPC .. *A61B 18/1442* (2013.01); *A61B 17/320092* (2013.01); *A61B 34/76* (2016.02);
(Continued)

(58) Field of Classification Search
    CPC A61B 2018/00791; A61B 2018/00797; A61B 2018/00809; A61B 2018/00815;
(Continued)

(56) References Cited

U.S. PATENT DOCUMENTS

| | | |
|---|---|---|
| 1,754,806 A | 4/1930 | Stevenson |
| 3,297,192 A | 1/1967 | Swett |

(Continued)

FOREIGN PATENT DOCUMENTS

| | | |
|---|---|---|
| CN | 101819334 A | 9/2010 |
| DE | 102008051866 | 10/2010 |

(Continued)

OTHER PUBLICATIONS

International Search Report dated Jan. 26, 2012 for Application No. PCT/US11/059220.
(Continued)

*Primary Examiner* — Jaymi Della
(74) *Attorney, Agent, or Firm* — Frost Brown Todd LLC

(57) ABSTRACT

A surgical instrument includes a temperature sensor and a control unit that is operable to deactivate an end effector of the surgical instrument. In some versions the temperature sensor detects the temperature of a transducer, while in others the temperature sensor detects the temperature of the end effector. The surgical instrument may also include a trigger and a trigger position sensor. A force sensor or a position sensor may be included to determine the force and/or position of the transmission assembly. The end effector may also include a force sensor or a micro coil. A surgical instrument having a sensor may be included in a surgical system that includes a control unit and a remote controller. In some instances the remote controller may have one or more force-feedback components. In addition, a device
(Continued)

interface and a surgeon interface may be included to remotely adjust the settings of the control unit.

18 Claims, 11 Drawing Sheets

Related U.S. Application Data

(60) Provisional application No. 61/410,603, filed on Nov. 5, 2010, provisional application No. 61/487,846, filed on May 19, 2011.

(51) Int. Cl.
  *A61B 34/00* (2016.01)
  *A61B 18/00* (2006.01)
  *A61B 17/00* (2006.01)
  *A61B 90/00* (2016.01)
  *A61B 34/30* (2016.01)

(52) U.S. Cl.
  CPC ...... *A61B 34/30* (2016.02); *A61B 2017/00039* (2013.01); *A61B 2017/00084* (2013.01); *A61B 2017/00119* (2013.01); *A61B 2017/00212* (2013.01); *A61B 2017/00398* (2013.01); *A61B 2018/00642* (2013.01); *A61B 2018/00773* (2013.01); *A61B 2018/00791* (2013.01); *A61B 2018/00988* (2013.01); *A61B 2018/1455* (2013.01); *A61B 2090/064* (2016.02)

(58) Field of Classification Search
  CPC .. A61B 2018/00821; A61B 17/320092; A61B 18/1442; A61B 19/2203; A61B 2017/00039; A61B 2017/00084; A61B 2017/00119; A61B 2017/00212; A61B 2017/00398; A61B 2018/1455; A61B 2019/2292; A61B 2019/464
  USPC .......................... 606/5–52, 205–211
  See application file for complete search history.

(56) References Cited

U.S. PATENT DOCUMENTS

| | | | |
|---|---|---|---|
| 3,419,198 A | 12/1968 | Pettersen | |
| 3,619,671 A | 11/1971 | Shoh | |
| 4,034,762 A | 7/1977 | Cosens et al. | |
| 4,057,220 A | 11/1977 | Kudlacek | |
| 4,535,773 A | 8/1985 | Yoon | |
| 4,641,076 A | 2/1987 | Linden et al. | |
| 4,662,068 A | 5/1987 | Polonsky | |
| 4,666,037 A | 5/1987 | Weissman | |
| 4,685,459 A * | 8/1987 | Koch et al. | 606/51 |
| 4,717,018 A | 1/1988 | Sacherer et al. | |
| 4,717,050 A | 1/1988 | Wright | |
| 4,721,097 A | 1/1988 | D'Amelio | |
| 4,768,969 A | 9/1988 | Bauer et al. | |
| 4,800,878 A | 1/1989 | Cartmell | |
| 4,844,259 A | 7/1989 | Glowczewskie, Jr. | |
| 4,878,493 A | 11/1989 | Pasternak et al. | |
| 5,071,417 A | 12/1991 | Sinofsky | |
| 5,107,155 A | 4/1992 | Yamaguchi | |
| 5,144,771 A | 9/1992 | Miwa | |
| 5,169,733 A | 12/1992 | Savovic et al. | |
| 5,176,677 A | 1/1993 | Wuchinich | |
| 5,246,109 A | 9/1993 | Markle et al. | |
| 5,273,177 A | 12/1993 | Campbell | |
| 5,277,694 A | 1/1994 | Leysieffer et al. | |
| 5,308,358 A | 5/1994 | Bond et al. | |
| 5,322,055 A | 6/1994 | Davison et al. | |
| 5,339,799 A | 8/1994 | Kami et al. | |
| 5,358,508 A | 10/1994 | Cobb et al. | |
| 5,361,902 A | 11/1994 | Abidin et al. | |
| 5,429,229 A | 7/1995 | Chester et al. | |
| 5,449,370 A | 9/1995 | Vaitekunas | |
| 5,454,378 A | 10/1995 | Palmer et al. | |
| 5,501,607 A | 3/1996 | Yoshioka et al. | |
| 5,507,297 A | 4/1996 | Slater et al. | |
| 5,561,881 A | 10/1996 | Klinger et al. | |
| 5,578,052 A | 11/1996 | Koros et al. | |
| 5,580,258 A | 12/1996 | Wakata | |
| 5,582,617 A | 12/1996 | Klieman et al. | |
| 5,590,778 A | 1/1997 | Dutchik | |
| 5,592,065 A | 1/1997 | Oglesbee et al. | |
| 5,599,350 A * | 2/1997 | Schulze et al. | 606/51 |
| 5,630,420 A | 5/1997 | Vaitekunas | |
| 5,630,456 A | 5/1997 | Hugo et al. | |
| 5,690,222 A | 11/1997 | Peters | |
| 5,707,369 A * | 1/1998 | Vaitekunas et al. | 606/31 |
| 5,741,305 A | 4/1998 | Vincent et al. | |
| 5,776,155 A | 7/1998 | Beaupre et al. | |
| 5,800,336 A | 9/1998 | Ball et al. | |
| 5,817,128 A | 10/1998 | Storz | |
| 5,868,244 A | 2/1999 | Ivanov et al. | |
| 5,873,873 A | 2/1999 | Smith et al. | |
| 5,882,310 A | 3/1999 | Marian, Jr. | |
| 5,935,144 A | 8/1999 | Estabrook | |
| 5,938,633 A | 8/1999 | Beupre | |
| 5,944,737 A | 8/1999 | Tsonton et al. | |
| 5,951,575 A | 9/1999 | Bolduc et al. | |
| 5,980,510 A | 11/1999 | Tsonton et al. | |
| 5,997,531 A | 12/1999 | Loeb et al. | |
| 6,018,227 A | 1/2000 | Kumar et al. | |
| 6,051,010 A | 4/2000 | Dimatteo et al. | |
| 6,056,735 A | 5/2000 | Okada et al. | |
| 6,063,098 A | 5/2000 | Houser et al. | |
| 6,066,151 A | 5/2000 | Miyawaki et al. | |
| 6,083,191 A | 7/2000 | Rose | |
| 6,083,223 A * | 7/2000 | Baker | 606/52 |
| 6,099,537 A | 8/2000 | Sugai et al. | |
| 6,113,593 A * | 9/2000 | Tu et al. | 606/34 |
| 6,123,702 A * | 9/2000 | Swanson et al. | 606/34 |
| 6,147,480 A | 11/2000 | Osadchy et al. | |
| 6,165,191 A | 12/2000 | Shibata et al. | |
| 6,190,386 B1 | 2/2001 | Rydell | |
| 6,204,592 B1 | 3/2001 | Hur | |
| 6,214,023 B1 | 4/2001 | Whipple et al. | |
| 6,246,896 B1 | 6/2001 | Dumoulin et al. | |
| 6,248,238 B1 | 6/2001 | Burtin et al. | |
| 6,287,304 B1 * | 9/2001 | Eggers et al. | 606/37 |
| 6,325,811 B1 | 12/2001 | Messerly | |
| 6,339,368 B1 | 1/2002 | Leith | |
| 6,398,755 B1 | 6/2002 | Belef et al. | |
| 6,409,742 B1 | 6/2002 | Fulton, III et al. | |
| 6,500,176 B1 | 12/2002 | Truckai et al. | |
| 6,500,188 B2 | 12/2002 | Harper et al. | |
| 6,512,667 B2 | 1/2003 | Shiue et al. | |
| 6,514,267 B2 | 2/2003 | Jewett | |
| 6,520,185 B1 | 2/2003 | Bommannan et al. | |
| 6,561,983 B2 | 5/2003 | Cronin et al. | |
| 6,562,032 B1 | 5/2003 | Ellman et al. | |
| 6,609,414 B2 | 8/2003 | Mayer et al. | |
| 6,623,500 B1 | 9/2003 | Cook et al. | |
| 6,626,901 B1 | 9/2003 | Treat et al. | |
| 6,647,281 B2 | 11/2003 | Morency | |
| 6,650,091 B1 | 11/2003 | Shiue et al. | |
| 6,650,975 B2 | 11/2003 | Ruffner | |
| 6,656,177 B2 | 12/2003 | Truckai et al. | |
| 6,658,301 B2 | 12/2003 | Loeb et al. | |
| 6,666,875 B1 | 12/2003 | Sakurai et al. | |
| 6,669,690 B1 | 12/2003 | Okada et al. | |
| 6,717,193 B2 | 4/2004 | Olewine et al. | |
| 6,730,042 B2 | 5/2004 | Fulton et al. | |
| 6,753,673 B2 | 6/2004 | Shiue et al. | |
| 6,758,855 B2 | 7/2004 | Fulton, III et al. | |
| 6,761,698 B2 | 7/2004 | Shibata et al. | |
| 6,761,701 B2 | 7/2004 | Cucin | |
| 6,783,524 B2 | 8/2004 | Anderson et al. | |
| 6,815,206 B2 | 11/2004 | Lin et al. | |
| 6,821,671 B2 | 11/2004 | Hinton et al. | |
| 6,836,097 B2 | 12/2004 | Turner et al. | |
| 6,838,862 B2 | 1/2005 | Luu | |

(56) References Cited

U.S. PATENT DOCUMENTS

| | | |
|---|---|---|
| 6,847,192 B2 | 1/2005 | Turner et al. |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 6,998,822 B2 | 2/2006 | Turner et al. |
| 7,031,155 B2 | 4/2006 | Sauciuc et al. |
| 7,061,749 B2 | 6/2006 | Liu et al. |
| 7,077,853 B2 | 7/2006 | Kramer et al. |
| 7,083,589 B2 | 8/2006 | Banko et al. |
| 7,085,123 B2 | 8/2006 | Shiue et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,186,473 B2 | 3/2007 | Shiue et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckal et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,560,903 B2 | 7/2009 | Thrap |
| 7,563,142 B1 | 7/2009 | Wenger et al. |
| 7,573,151 B2 | 8/2009 | Acena et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,658,247 B2 | 2/2010 | Carter |
| 7,692,411 B2 | 4/2010 | Trainor et al. |
| 7,717,312 B2 | 5/2010 | Beetel |
| 7,721,936 B2 | 5/2010 | Shelton, IV et al. |
| 7,738,971 B2 | 6/2010 | Swayze et al. |
| 7,761,198 B2 | 7/2010 | Bhardwaj |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,776,037 B2 | 8/2010 | Odom |
| 7,780,660 B2 | 8/2010 | Bourne et al. |
| 7,802,121 B1 | 9/2010 | Zansky et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,913,891 B2 | 3/2011 | Doll et al. |
| 7,922,063 B2 | 4/2011 | Zemlok et al. |
| 7,923,151 B2 | 4/2011 | Lam et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 7,977,921 B2 | 7/2011 | Bahai et al. |
| 7,982,439 B2 | 7/2011 | Trainor et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,083,120 B2 | 12/2011 | Shelton et al. |
| 8,097,011 B2 | 1/2012 | Hideo et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,267,094 B2 | 9/2012 | Danek et al. |
| 8,277,446 B2 | 10/2012 | Heard |
| 8,292,888 B2 | 10/2012 | Whitman |
| 8,298,253 B2 | 10/2012 | Charles |
| 8,301,262 B2 | 10/2012 | Mi et al. |
| 8,336,725 B2 | 12/2012 | Ramsey et al. |
| 8,344,690 B2 | 1/2013 | Smith et al. |
| 8,377,059 B2 | 2/2013 | Deville et al. |
| 8,400,108 B2 | 3/2013 | Powell et al. |
| 8,419,758 B2 | 4/2013 | Smith et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,550,106 B2 | 10/2013 | Hebach et al. |
| 8,551,088 B2 | 10/2013 | Falkenstein et al. |
| 8,564,242 B2 | 10/2013 | Hansford et al. |
| 8,573,461 B2 | 11/2013 | Shelton et al. |
| 8,617,077 B2 | 12/2013 | van Groningen et al. |
| 8,641,629 B2 | 2/2014 | Kurokawa |
| 8,663,112 B2 | 3/2014 | Slayton et al. |
| 2001/0032666 A1 | 10/2001 | Jenson et al. |
| 2002/0133148 A1* | 9/2002 | Daniel et al. .................. 606/34 |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0144680 A1 | 7/2003 | Kellogg et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton et al. |
| 2005/0070958 A1* | 3/2005 | Swayze et al. ............... 606/219 |
| 2005/0171522 A1* | 8/2005 | Christopherson ............ 606/34 |
| 2005/0256522 A1* | 11/2005 | Francischelli et al. ......... 606/41 |
| 2006/0030797 A1 | 2/2006 | Zhou et al. |
| 2006/0079829 A1 | 4/2006 | Fulton et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0074719 A1* | 4/2007 | Danek et al. ............. 128/200.24 |
| 2007/0078484 A1 | 4/2007 | Talarico et al. |
| 2007/0084742 A1 | 4/2007 | Miller et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0239028 A1 | 10/2007 | Houser et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |

(56) References Cited

U.S. PATENT DOCUMENTS

| | | |
|---|---|---|
| 2008/0255413 A1 | 10/2008 | Zemlok et al. |
| 2008/0281301 A1 | 11/2008 | Deboer et al. |
| 2008/0315829 A1 | 12/2008 | Jones et al. |
| 2009/0030437 A1 | 1/2009 | Houser et al. |
| 2009/0036914 A1 | 2/2009 | Houser |
| 2009/0043797 A1 | 2/2009 | Dorie et al. |
| 2009/0076506 A1 | 3/2009 | Baker |
| 2009/0096430 A1 | 4/2009 | Van Der Linde et al. |
| 2009/0105750 A1 | 4/2009 | Price et al. |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0171354 A1* | 7/2009 | Deville et al. .......... 606/51 |
| 2009/0209979 A1 | 8/2009 | Yates et al. |
| 2009/0209990 A1 | 8/2009 | Yates et al. |
| 2009/0240246 A1 | 9/2009 | Deville et al. |
| 2009/0253030 A1 | 10/2009 | Kooij |
| 2009/0264940 A1 | 10/2009 | Beale |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1 | 2/2010 | Prevost |
| 2010/0060231 A1 | 3/2010 | Trainor et al. |
| 2010/0069940 A1 | 3/2010 | Miller et al. |
| 2010/0076455 A1 | 3/2010 | Birkenbach et al. |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Alexander et al. |
| 2010/0211053 A1 | 8/2010 | Ross et al. |
| 2010/0249665 A1 | 9/2010 | Roche |
| 2010/0256635 A1* | 10/2010 | McKenna et al. .......... 606/45 |
| 2010/0268221 A1 | 10/2010 | Beller et al. |
| 2010/0274160 A1 | 10/2010 | Yachi et al. |
| 2010/0301095 A1 | 12/2010 | Shelton, IV et al. |
| 2011/0009694 A1 | 1/2011 | Schultz et al. |
| 2011/0015660 A1 | 1/2011 | Wiener et al. |
| 2011/0058982 A1 | 3/2011 | Kaneko et al. |
| 2011/0074336 A1 | 3/2011 | Miller |
| 2011/0077514 A1 | 3/2011 | Ulric et al. |
| 2011/0080134 A1 | 4/2011 | Miller |
| 2011/0087212 A1 | 4/2011 | Aldridge et al. |
| 2011/0087218 A1 | 4/2011 | Boudreaux et al. |
| 2011/0152901 A1 | 6/2011 | Woodruff et al. |
| 2011/0221398 A1 | 9/2011 | Ferber |
| 2011/0224668 A1 | 9/2011 | Johnson et al. |
| 2011/0288573 A1 | 11/2011 | Yates et al. |
| 2012/0179036 A1 | 7/2012 | Patrick et al. |
| 2012/0265230 A1 | 10/2012 | Laurent et al. |
| 2012/0283732 A1 | 11/2012 | Lam |
| 2012/0292367 A1 | 11/2012 | Morgan et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090530 A1 | 4/2013 | Ramamurthy et al. |
| 2013/0090552 A1 | 4/2013 | Ramamurthy et al. |
| 2013/0116690 A1 | 5/2013 | Unger |
| 2013/0118733 A1 | 5/2013 | Kumar |
| 2013/0342962 A1 | 12/2013 | Fletcher et al. |
| 2014/0088379 A1 | 3/2014 | Bhamra et al. |

FOREIGN PATENT DOCUMENTS

| | | |
|---|---|---|
| DE | 102009013034 | 10/2010 |
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| JP | 2000-210301 A | 8/2000 |
| JP | 3989121 B | 10/2000 |
| JP | 4145069 B | 10/2003 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/096025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

International Search Report dated Feb. 1, 2012 for Application No. PCT/US11/059223.

International Search Report dated Jan. 12, 2012 for Application No. PCT/US11/059226.

International Search Report dated May 29, 2012 for Application No. PCT/US11/059358.

Restriction Requirement dated Dec. 11, 2012 for U.S. Appl. No. 13/151,481.

Office Action Non-Final dated Feb. 15, 2013 for U.S. Appl. No. 13/151,481.

Office Action Final dated Jun. 7, 2013 for U.S. Appl. No. 13/151,481.

Restriction Requirement dated Mar. 13, 2013 for U.S. Appl. No. 13/151,509.

Retriction Requirement dated Feb. 28, 2013 for U.S. Appl. No. 13/270,667.

Office Action Non-Final dated Apr. 26, 2013 for U.S. Appl. No. 13/270,667.

Office Action Non-Final dated Dec. 12, 2012 for U.S. Appl. No. 13/274,516.

(56) References Cited

OTHER PUBLICATIONS

Restriction Requirement dated Feb. 25, 2013 for U.S. Appl. No. 13/274,540.
Office Action Non-Final dated Apr. 30, 2013 U.S. Appl. No. 13/274,540.
Office Action Non-Final dated Apr. 1, 2013 for U.S. Appl. No. 13/274,805.
Restriction Requirement dated Apr. 29, 2013 for U.S. Appl. No. 13/274,830.
Restriction Requirment dated Apr. 4, 2013 for U.S. Appl. No. 13/275,495.
Office Action Non-Final May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Restriction Requirement dated Feb. 6, 2013, for U.S. Appl. No. 13/276,660.
Office Action Non-Final dated Jun. 3, 2013 for U.S. Appl. No. 13/246,660.
Office Action Non-Final dated Dec. 21, 2012 for U.S. Appl. No. 13/276,673.
Restriction Requirement dated Feb. 6, 2013 for U.S. Appl. No. 13/276,687.
Restriction Requirement dated Feb. 21, 2013 U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
U.S. Appl. No. 13/151,471, filed Jun. 2, 2011, Stulen.
U.S. Appl. No. 13/151,481, filed Jun. 2, 2011, Yates et al.
U.S. Appl. No. 13/151,488, filed Jun. 2, 2011, Shelton IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011 Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.

Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
EP Communication dated Feb. 19, 2014 for Application No. EP 11781972.2.
International Preliminary Report on Patentability dated May 7, 2013 for Application No. PCT/US2011/059212.
International Preliminary Report on Patentability dated May 8, 2013 for Application No. PCT/US2011/059215.
International Preliminary Report on Patentability dated May 7, 2013 for Application No. PCT/US2011/059217.
International Preliminary Report on Patentability dated May 7, 2013 for Application No. PCY/US2011/059218.
International Preliminary Report on Patentability dated May 7, 2013 for Application No. PCT/US2011/059220.
International Preliminary Report on Patentability dated May 7, 2013 for Application No. PCT/US2011/059222.
International Preliminary Report on Patentability dated Feb. 1, 2012 for Application No. PCT/US2011/059223.
International Preliminary Report on Patentability dated May 7, 2013 for Application No. PCT/US2011/059226.
International Preliminary Report on Patentability dated May 7, 2013 for Application No. PCT/US2011/059338.
International Preliminary Report on Patentability dated May 7, 2013 for Application No. PCT/US2011/059351.
International Preliminary Report on Patentability dated May 7, 2013 for Application No. PCT/US2011/059354.
International Preliminary Report on Patentability dated May 7, 2013 for Application No. PCT/US2011/059358.
International Preliminary Report on Patentability dated May 7, 2013 for Application No. PCT/US2011/059362.
International Preliminary Report on Patentability dated May 8, 2013 for Application No. PCT/US2011/059365.
International Preliminary Report on Patentability dated May 7, 2013 for Application No. PCT/US2011/059371.
International Preliminary Report on Patentability dated May 7, 2013 for Application No. PCT/US2011/059378.
International Preliminary Report on Patentability dated May 8, 2013 for Application No. PCT/US2011/059381.
US Office Action, Non-Final, dated Dec. 6, 2013 for U.S. Appl. No. 13/151,471.
US Office Action, Non-Final, dated Mar. 28, 2014 for U.S. Appl. No. 13/151,471.
US Office Action, Notice of Allowance, dated Aug. 19, 2014 for U.S. Appl. No. 13/151,471.
US Office Action, Notice of Allowance, dated Nov. 21, 2014 for U.S. Appl. No. 13/151,471.
US Office Action, Non-Final, dated Aug. 14, 2014 for U.S. Appl. No. 13/151,481.
US Office Action, Non-Final, dated Nov. 7, 2014 for U.S. Appl. No. 13/151,488.
US Office Action, Final, dated Nov. 21, 2013 for U.S. Appl. No. 13/151,498.
US Office Action, Non-Final, dated Mar. 18, 2014 for U.S. Appl. No. 13/151,498.
US Office Action, Notice of Allowance, dated Aug. 6, 2014 for U.S. Appl. No. 13/151,498.
US Office Action, Notice of Allowance, dated Nov. 21, 2014 for U.S. Appl. No. 13/151,498.
US Office Action, Non-Final, dated Jun. 18, 2014 for U.S. Appl. No. 13/151,503.
US Office Action, Non-Final, dated Nov. 6, 2014 for U.S. Appl. No. 13/151,503.
US Office Action, Non-Final, dated Sep. 26, 2013 for U.S. Appl. No. 13/151,509.
US Office Action, Final, dated Jan. 29, 2014 for U.S. Appl. No. 13/151,509.
US Office Action, Non-Final, dated Jul. 9, 2014 for U.S. Appl. No. 13/151,509.
US Office Action, Notice of Allowance, dated Oct. 28, 2014 for U.S. Appl. No. 13/151,509.

(56) References Cited

OTHER PUBLICATIONS

US Office Action, Restriction Requirement, dated Jun. 11, 2014 for U.S. Appl. No. 13/151,512.
US Office Action, Notice of Allowance, dated Oct. 29, 2014 for U.S. Appl. No. 13/151,512.
US Office Action, Restriction Requirement, dated Jul. 11, 2014 for U.S. Appl. No. 13/269,870.
US Office Action, Final, dated Oct. 25, 2013 for U.S. Appl. No. 13/270,667.
US Office Action, Non-Final, dated Jul. 29, 2014 for U.S. Appl. No. 13/270,667.
US Office Action, Restriction Requirement, dated Jul. 9, 2014 for U.S. Appl. No. 13/270,684.
US Office Action, Non-Final, dated Oct. 9, 2014 for U.S. Appl. No. 13/270,684.
US Office Action, Restriction Requirement, dated Sep. 11, 2014 for U.S. Appl. No. 13/270,701.
US Office Action, Non-Final, dated Nov. 21, 2013 for U.S. Appl. No. 13/271,352.
US Office Action, Restriction Requirement, dated Sep. 25, 2014 for U.S. Appl. No. 13/271,352.
US Office Action, Restriction Requirement, dated Oct. 2, 2013 for U.S. Appl. No. 13/274,480.
US Office Action, Non-Final, dated Feb. 14, 2014 for U.S. Appl. No. 13/274,480.
US Office Action, Final, dated Jul. 17, 2014 for U.S. Appl. No. 13/274,480.
US Office Action, Restriction Requirement, dated Dec. 9, 2013 for U.S. Appl. No. 13/274,496.
US Office Action, Non-Final, dated Feb. 6, 2014 for U.S. Appl. No. 13/274,496.
US Office Action, Final, dated May 15, 2014 for U.S. Appl. No. 13/274,496.
US Office Action, Final, dated Aug. 22, 2014 for U.S. Appl. No. 13/274,496.
US Office Action, Restriction Requirement, dated Mar. 28, 2014 for U.S. Appl. No. 13/274,507.
US Office Action, Non-Final, dated Jun. 19, 2014 for U.S. Appl. No. 13/274,507.
US Office Action, Non-Final, dated Dec. 6, 2013 for U.S. Appl. No. 13/274,516.
US Office Action, Final, dated Jun. 12, 2014 for U.S. Appl. No. 13/274,516.
US Office Action, Non-Final, dated Oct. 8, 2014 for U.S. Appl. No. 13/274,516.
US Office Action, Final, dated Oct. 25, 2013 for U.S. Appl. No. 13/274,540.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Final, dated Nov. 26, 2013 for U.S. Appl. No. 13/274,830.
US Office Action, Non-Final, dated Oct. 22, 2014 for U.S. Appl. No. 13/274,830.
US Office Action, Final, dated Dec. 5, 2013 for U.S. Appl. No. 13/275,495.
US Office Action, Non-Final, dated Jan. 6, 2014 for U.S. Appl. No. 13/275,514.
US Office Action, Non-Final, dated Sep. 9, 2014 for U.S. Appl. No. 13/275,514.
US Office Action, Final, dated Feb. 28, 2014 for U.S. Appl. No. 13/275,547.
US Office Action, Non-Final, dated Aug. 20, 2014 for U.S. Appl. No. 13/275,547.
US Office Action, Non-Final, dated Oct. 23, 2014 for U.S. Appl. No. 13/275,563.
US Office Action, Restriction Requirement, dated Jul. 9, 2014 for U.S. Appl. No. 13/276,660.
US Office Action, Final, dated Mar. 21, 2014 for U.S. Appl. No. 13/276,673.
US Office Action, Non-Final, dated Aug. 14, 2014 for U.S. Appl. No. 13/276,673.
US Office Action, Notice of Allowance, dated Nov. 12, 2013 for U.S. Appl. No. 13/276,687.
US Office Action, Notice of Allowance, dated Jun. 2, 2014 for U.S. Appl. No. 13/276,687.
US Office Action, Notice of Allowance, dated Sep. 12, 2014 for U.S. Appl. No. 13/276,687.
US Office Action, Final, dated Sep. 27, 2013 for U.S. Appl. No. 13/276,707.
US Office Action, Non-Final, dated Aug. 20, 2014 for U.S. Appl. No. 13/276,725.
US Office Action, Final, dated Nov. 8, 2013 for U.S. Appl. No. 13/276,745.
US Office Action, Non-Final, dated Feb. 28, 2014 for U.S. Appl. No. 13/276,745.
US Office Action, Notice of Allowance, dated Oct. 7, 2014 for U.S. Appl. No. 13/276,745.
International Search Report dated Jan. 26, 2012 for U.S. Appl. No. PCT/US2011/059220.
International Search Report dated Jul. 6, 2012 for U.S. Appl. No. PCT/US2011/059381.
Restriction Requirement dated Feb. 28, 2013 for U.S. Appl. No. 13/270,667.
Office Action Non-Final dated Jun. 14, 2013 for U.S. Appl. No. 13/151,498.
Office Action Non-Final dated Jun. 12, 2013 for U.S. Appl. No. 13/276,687.
Office Action Non-Final dated Jun. 14, 2013 for U.S. Appl. No. 13/274,830.
Restriction Requirement dated Jun. 24, 2013 for U.S. Appl. No. 13/151,509.
Restriction Requirement dated Jul. 5, 2013 for U.S. Appl. No. 13/151,488.
Office Action Non-Final dated Aug. 6, 2013 for U.S. Appl. No. 13/151,471.
Office Action Final dated Aug. 16, 2013 for U.S. Appl. No. 13/274,516.
Office Action Non-Final dated Aug. 19, 2013 for U.S. Appl. No. 13/276,673.
Office Action Final dated Aug. 29, 2013 for U.S. Appl. No. 13/275,563.
Office Action Final dated Sep. 12, 2013 for U.S. Appl. No. 13/274,805.
US Office Action, Notice of Allowance, dated Feb. 25, 2015 for U.S. Appl. No. 13/151,509.
US Office Action, Notice of Allowance, dated Feb. 17, 2015 for U.S. Appl. No. 13/151,512.
US Office Action, Non-Final, dated Jan. 5, 2015 for U.S. Appl. No. 13/269,870.
US Office Action, Notice of Allowance, dated Dec. 17, 2014 for U.S. Appl. No. 13/270,667.
US Office Action, Non-Final, dated Dec. 16, 2014 for U.S. Appl. No. 13/270,701.
US Office Action, Restriction Requirement, dated Feb. 25, 2015 for U.S. Appl. No. 13/271,364.
US Office Action, Notice of Allowance, dated Jan. 21, 2015 for U.S. Appl. No. 13/274,540.
US Office Action, Notice of Allowance, dated Nov. 28, 2014 for U.S. Appl. No. 13/274,805.
US Office Action, Notice of Allowance, dated Jan. 21, 2015 for U.S. Appl. No. 13/274,805.
US Office Action, Non-Final, dated Feb. 25, 2015 for U.S. Appl. No. 13/275,495.
US Office Action, Notice of Allowance, dated Dec. 23, 2014 for U.S. Appl. No. 13/276,687.
US Office Action, Non-Final, dated Jan. 29, 2015 for U.S. Appl. No. 13/276,707.
US Office Action, Notice of Allowance, dated Dec. 19, 2014 for U.S. Appl. No. 13/276,745.
U.S. Appl. No. 61/410,603, filed Nov. 5, 2010.

(56) References Cited

OTHER PUBLICATIONS

International Search Report and Written Opinion dated Jan. 26, 2012 for Application No. PCT/US2011/059212.
International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012 for Application No. PCT/US2011/059362.
Communication from International Searching Authority dated Feb. 2, 2012 for Application No. PCT/US2011/059222.
Communication from International Searching Authority dated Jan. 24, 2012 for Application No. PCT/US2011/059215.
Communication from International Searching Authority dated Feb. 2, 2012 for Application No. PCT/US2011/059378.
Machine Translation of the Abstract of German Application No. DE 102009013034.
Machine Translation of German Application No. DE 102008051866.
Chinese Second Office Action dated Aug. 4, 2015 for Application No. CN 2011800641486.
Australian First Examination Report dated Jun. 17, 2015 for Application No. AU 2011323279.
Australian First Examination Report dated May 18, 2015 for Application No. AU 2011323284.
Chinese First Office Action dated Jul. 1, 2015 for Application No. CN 201180063986.1.
Chinese First Office Action dated Mar. 27, 2015 for Application No. CN 2011800638214.
Chinese First Office Action dated Jan. 29, 2015 for Application No. CN 2011800638159.
Chinese First Office Action dated Mar. 4, 2015 for Application No. CN 201180063595X.
U.S. Office Action, Final, dated Apr. 1, 2015 for U.S. Appl. No. 13/151,481.
U.S. Office Action, Notice of Allowance, dated Jun. 10, 2015 for U.S. Appl. No. 13/151,481.
U.S. Office Action-Non, Final, dated May 1, 2015 for U.S. Appl. No. 13/274,480.
U.S. Office Action, Notice of Allowance, dated Jun. 17, 2015 for U.S. Appl. No. 13/276,660.
U.S. Office Action, Final, dated Mar. 13, 2015 for U.S. Appl. No. 13/276,673.
Japanese Office Action, Notification of Reasons for Refusal, dated Sep. 8, 2015 for Application No. 2013-537829.
Japanese Office Action, Notification of Reasons for Refusal, dated Jul. 5, 2016 for Application No. 2013-537829.
Japanese Office Action, Notification of Reasons for Refusal, dated Sep. 29, 2015 for Application No. 2013-537877.

\* cited by examiner

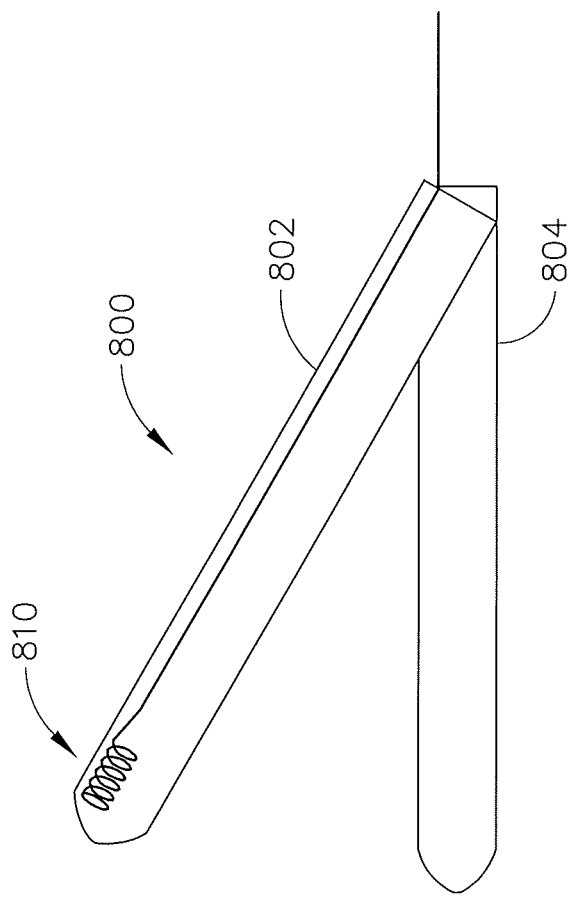

ND POWERED CONTROL

SURGICAL INSTRUMENT WITH SENSOR AND POWERED CONTROL

PRIORITY

This application is a continuation-in-part of U.S. patent application Ser. No. 13/151,481, entitled "Motor Driven Electrosurgical Device with Mechanical and Electrical Feedback," filed Jun. 2, 2011, published as U.S. Pat. Pub. No. 2012/0116379 on May 10, 2012, now U.S. Pat. No. 9,161,803, issued on Oct. 20, 2014, the disclosure of which is incorporated by reference herein.

This application also claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued on Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 16, 2013, the disclosure of which is incorporated by reference herein.

In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 10 depicts a side elevation view of an end effector having an exemplary micro coil.

Figure 1:
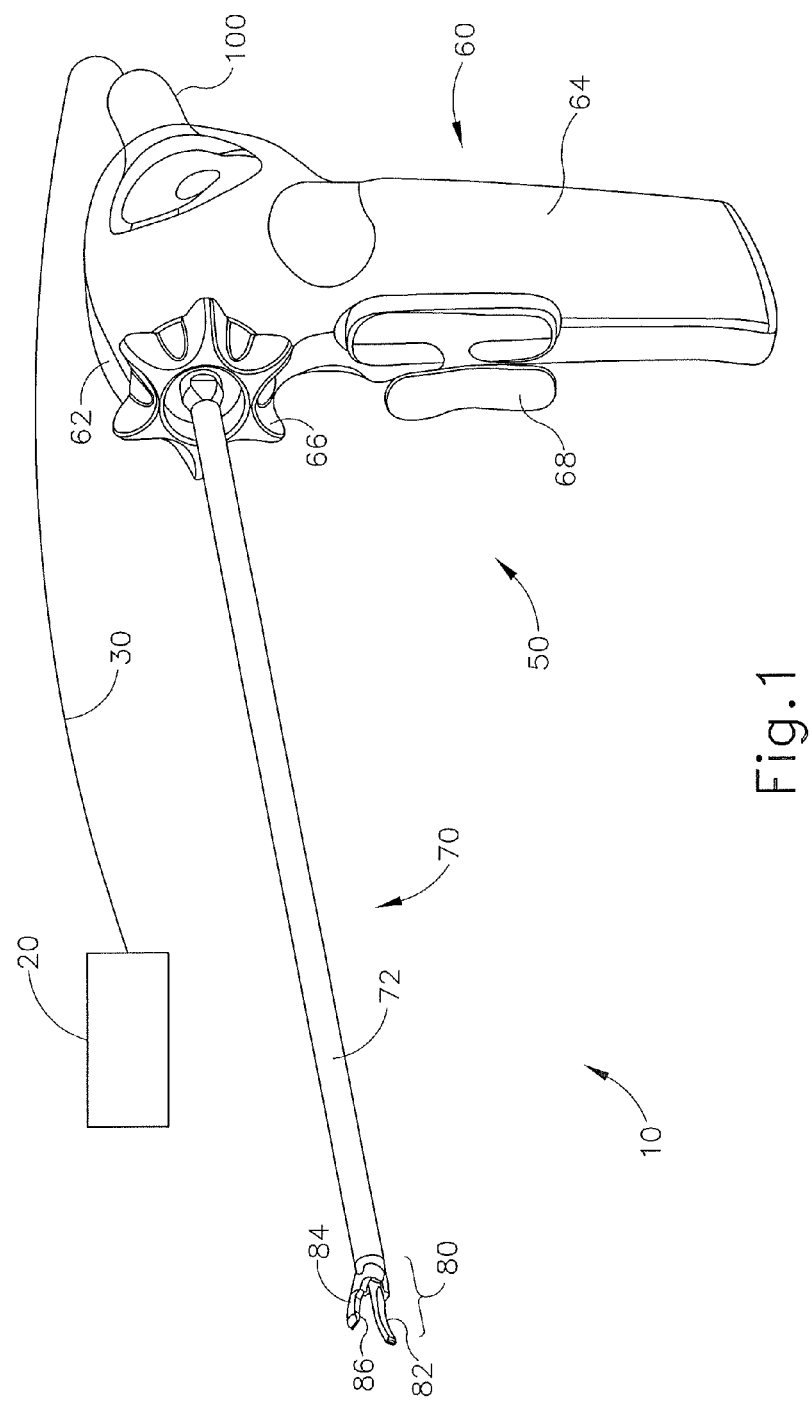
FIG. 1 depicts a perspective view of an exemplary ultrasonic surgical system comprising a surgical instrument and a generator.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Ultrasonic Surgical System

FIG. 1 shows an exemplary ultrasonic surgical system (10) comprising an ultrasonic surgical instrument (50), a generator (20), and a cable (30) operable to couple generator (20) to surgical instrument (50). A suitable generator (20) is the GEN 300 sold by Ethicon Endo-Surgery, Inc. of Cincinnati, Ohio. In some versions, generator (20) is constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein. It should be noted that surgical instrument (50) will be described in reference to an ultrasonic surgical instrument; however, the technology described below may be used with a variety of surgical instruments, including, but not limited to, endocutters, graspers, cutters, staplers, clip appliers, access devices, drug/gene therapy delivery devices, and energy delivery devices using ultrasound, RF, laser, etc., and/or any combination thereof as will be apparent to one of ordinary skill in the art in view of the teachings herein. Moreover, while the present example will be described in reference to a cable-connected surgical instrument (50), it should be understood that surgical instrument (50) may be adapted for cordless operation, such as that disclosed in U.S. Pat. Pub. No. 2009/0143797, entitled "Cordless Hand-held Ultrasonic Cautery Cutting Device," published Jun. 4, 2009, issued as U.S. Pat. No. 8,419,757 on Apr. 16, 2013, the disclosure of which is incorporated by reference herein. Furthermore, surgical instrument (50) may also be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004.

Surgical instrument (50) of the present example includes a multi-piece handle assembly (60), an elongated transmission assembly (70), and a transducer (100). Transmission assembly (70) is coupled to multi-piece handle assembly (60) at a proximal end of transmission assembly (70) and extends distally from multi-piece handle assembly (60). In the present example transmission assembly (70) is configured to be an elongated, thin tubular assembly for endoscopic use, but it should be understood that transmission assembly (70) may alternatively be a short assembly, such as those disclosed in U.S. Pat. Pub. No. 2007/0282333, entitled "Ultrasonic Waveguide and Blade," published Dec. 6, 2007, now abandoned, and U.S. Pat. Pub. No. 2008/0200940, entitled "Ultrasonic Device for Cutting and Coagulating," published Aug. 21, 2008, now abandoned, the disclosures of which are incorporated by reference herein. Transmission assembly (70) of the present example comprises an outer sheath (72), an inner tubular actuating member (not shown), a waveguide (not shown), and an end effector (80) located on the distal end of transmission assembly (70). In the present example, end effector (80) comprises a blade (82) coupled to the waveguide, a clamp arm (84) operable to pivot at the proximal end of transmission assembly (70), and, optionally, one or more clamp pads (86) coupleable to clamp arm (84). It should also be understood that clamp arm (84) and associated features may be constructed and operable in accordance with at least some of the teachings of U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein.

The waveguide, which is adapted to transmit ultrasonic energy from a transducer (100) to blade (82), may be flexible, semi-flexible, or rigid. One merely exemplary ultrasonic transducer (100) is Model No. HP054, sold by Ethicon Endo-Surgery, Inc. of Cincinnati, Ohio. The waveguide may also be configured to amplify the mechanical vibrations transmitted through the waveguide to blade (82) as is well known in the art. The waveguide may further have features to control the gain of the longitudinal vibration along the waveguide and features to tune the waveguide to the resonant frequency of the system.

In the present example, the distal end of the blade (82) is disposed near an anti-node in order to tune the acoustic assembly to a preferred resonant frequency $f_o$ when the acoustic assembly is not loaded by tissue. When transducer (100) is energized, the distal end of blade (82) is configured to move longitudinally in the range of, for example, approximately 10 to 500 microns peak-to-peak, and preferably in the range of about 20 to about 200 microns at a predetermined vibratory frequency $f_o$ of, for example, 55.5 kHz. When transducer (100) of the present example is activated, these mechanical oscillations are transmitted through the waveguide to end effector (80). In the present example, blade (82), being coupled to the waveguide, oscillates at the ultrasonic frequency. Thus, when tissue is secured between blade (82) and clamp arm (84), the ultrasonic oscillation of blade (82) may simultaneously sever the tissue and denature the proteins in adjacent tissue cells, thereby providing a coagulative effect with relatively little thermal spread. An electrical current may also be provided through blade (82) and clamp arm (84) to also cauterize the tissue. While some configurations for transmission assembly (70) and transducer (100) have been described, still other suitable configurations for transmission assembly (70) and transducer (100) will be apparent to one or ordinary skill in the art in view of the teachings herein.

Multi-piece handle assembly (60) of the present example comprises a mating housing portion (62) and a lower portion (64). Mating housing portion (62) is configured to receive transducer (100) at a proximal end of mating housing portion (62) and to receive the proximal end of transmission assembly (70) at a distal end of mating housing portion (62). An aperture is provided on the distal end of mating housing portion (62) for insertion of various transmission assemblies (70). A rotation knob (66) is shown in the present example to rotate transmission assembly (70) and/or transducer (100), but it should be understood that rotation knob (66) is merely optional. Lower portion (64) of multi-piece handle assembly (60) includes a trigger (68) and is configured to be grasped by a user using a single hand. One merely exemplary alternative configuration for lower portion (64) is depicted in FIG. 1 of U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein.

Toggle buttons (not shown) may be located on a distal surface of lower portion (64) and may be operable to activate transducer (100) at different operational levels using generator (20). For instance, a first toggle button may activate transducer (100) at a maximum energy level while a second toggle button may activate transducer (100) at a minimum, non-zero energy level. Of course, the toggle buttons may be configured for energy levels other than a maximum and/or minimum energy level as will be apparent to one of ordinary skill in the art in view of the teachings herein. Moreover, the toggle buttons may be located anywhere else on multi-piece handle assembly (60), on transducer (100), and/or remote from surgical instrument (50), and any number of toggle buttons may be provided.

While multi-piece handle assembly (60) has been described in reference to two distinct portions (62, 64), it should be understood that multi-piece handle assembly (60) may be a unitary assembly with both portions (62, 64) combined. Multi-piece handle assembly (60) may alternatively be divided into multiple discrete components, such as a separate trigger portion (operable either by a user's hand or foot) and a separate mating housing portion (62). The trigger portion may be operable to activate transducer (100) and may be remote from mating housing portion (62). Multi-piece handle assembly (60) may be constructed from a durable plastic (such as polycarbonate or a liquid crystal polymer), ceramics and/or metals or any other suitable material as will be apparent to one of ordinary skill in the art in view of the teachings herein. Still other configurations for multi-piece handle assembly (60) will be apparent to those of ordinary skill in the art in view of the teachings herein. For instance, instrument (50) may be operated as part of a robotic system. Other configurations for multi-piece handle assembly (60) will also be apparent to those of ordinary skill in the art in view of the teachings herein. By way of example only, surgical instrument (50) may be constructed in accordance with at least some of the teachings of U.S. Pat. Pub. No. 2006/0079874, now abandoned; U.S. Pat. Pub. No. 2007/0191713, now abandoned; U.S. Pat. Pub. No. 2007/0282333, now abandoned; U.S. Pat. Pub. No. 2008/0200940, now abandoned; U.S. Pat. Pub. No. 2011/0015660, issued as U.S. Pat. No. 8,461,744 on Jun. 11, 2013; U.S. Pat. No. 6,500,176; U.S. Pat. Pub. No. 2011/0087218, now U.S. Pat. No. 8,939,974, issued on Jan. 27, 2015; and/or U.S. Pat. Pub. No. 2009/0143797 issued as U.S. Pat. No. 8,419,757 on Apr. 16, 2013.

Additional configurations for surgical instrument (50) may be described in more detail in U.S. patent application Ser. No. 13/269,899, entitled "Ultrasonic Surgical Instrument with Modular End Effector," filed Oct. 10, 2011, now U.S. Pat. No. 9,050,125, issued on Jun. 9, 2015, the disclosure of which is incorporated by reference herein.

A. Exemplary Ultrasonic Surgical Instrument Handle Assembly with Sensors

In some versions it may be useful to include sensors to monitor the status of surgical instrument (50) and/or the components therein. For instance, a user may desire to monitor the temperature of transducer (100) and/or end effector (80). In addition, the user may desire to monitor the position and/or orientation of end effector (80) relative to one or more predetermined positions. Such positional and/or orientation monitoring may permit the user to monitor their use of surgical instrument (50) remotely (e.g., graphically on a monitor or otherwise) or may permit a device to provide feedback to the user based upon the positional and/or orientation information of surgical instrument (50). Alternatively, such positional and/or orientation monitoring may be used by a robotic device to monitor the movement of surgical instrument (50) or by a user controlling surgical instrument (50) remotely. Accordingly, various sensors for surgical instruments will be described herein.

Figure 2:
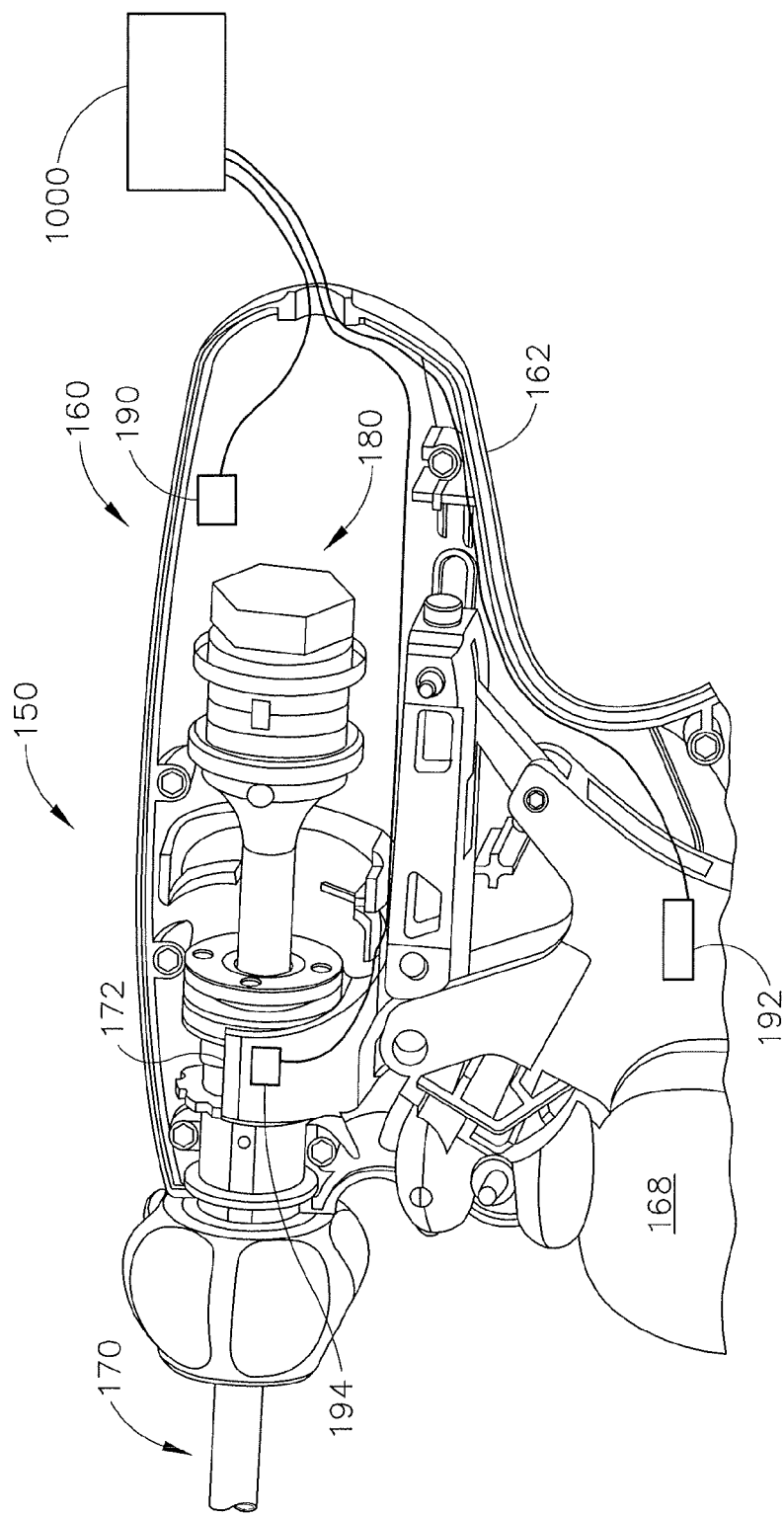
FIG. 2 depicts a side perspective view of an exemplary handle assembly having a transducer and a plurality of sensors therein.

FIG. 2 depicts a surgical instrument (150) having a multi-piece handle assembly (160), an elongated transmission assembly (170), and a transducer (180). Multi-piece handle assembly (160), elongated transmission assembly (170), and transducer (180) may be constructed in accordance with at least some of the teachings of multi-piece handle assembly (60), transmission assembly (70), and/or transducer (100) described above. In the present example, a transducer temperature sensor (190) is coupled to an interior surface of a casing (162) at a position that is substantially near transducer (180). In other versions, transducer temperature sensor (190) is coupled to transducer (180) or contained on or within a casing of transducer (180). Transducer temperature sensor (190) is operable to measure the temperature of transducer (180) or of the atmosphere near transducer (180). For instance, transducer temperature sensor (190) may comprise a thermocouple or a thermistor. In some versions transducer temperature sensor (190) is configured to have a positive temperature coefficient (PTC), while in others, transducer temperature sensor (190) is configured to have a negative temperature coefficient (NTC). Of course other configurations for transducer temperature sensor (190) will be apparent to one of ordinary skill in the art in view of the teachings herein. Transducer temperature sensor (190) of the present example is communicatively coupled to a control unit (1000) such that transducer temperature sensor (190) may communicate the temperature signals to control unit (1000), as will be described in greater detail below.

Surgical instrument (150) of the present example further includes a trigger position sensor (192) coupled to casing (162). Trigger position sensor (192) of the present example comprises an optical diode switch, though other position sensors may be used as well, such as optical encoders, magnetic encoders, resistive encoders, etc. Trigger position sensor (192) is operable to determine the position of a trigger (168) relative to casing (162). Trigger position sensor (192) is also communicatively coupled to control unit (1000) such that trigger position sensor (192) may communicate signals indicative of the position of trigger (168). Of course other configurations for trigger position sensor (192) will be apparent to one of ordinary skill in the art in view of the teachings herein. For instance, a plurality of trigger position sensors (192) may be included to further refine the determination of the position of trigger (168) relative to casing (162). By way of example only, a plurality of optical diode switches may be used such that a series of optical switches are tripped as trigger (168) is pivoted.

In the present example, trigger (168) is configured to longitudinally actuate a yoke (172) when trigger (168) is actuated by a user. Yoke (172) is coupled to an inner tubular actuation member (not shown) that actuates a clamp arm (not shown) of an end effector (not shown). The inner tubular actuation member, clamp arm, and end effector will be described in greater detail in reference to FIGS. 3A-3B. Yoke (172) of the present example further includes a yoke sensor (194). Yoke sensor (194) comprises a strain gauge that is operable to determine the force yoke (172) is applying to the inner tubular actuation member. The strain gauge may be calibrated against a known standard prior to being coupled to yoke (172). In the example shown, yoke sensor (194) is coupled to a side of yoke (172), though in other versions yoke sensor (194) may be located on a distal end of yoke (172) or between yoke (172) and the portion of the inner tubular actuation member that yoke (172) engages. Yoke sensor (194) is also communicatively coupled to control unit (1000) such that yoke sensor (194) may communicate the signal representative of the force on yoke (172) to control unit (1000). Of course other configurations for yoke sensor (194) will be apparent to one of ordinary skill in the art in view of the teachings herein.

Control unit (1000) comprises an integrated circuit or a microcontroller configured to receive input from one or more sensors and output control instructions to one or more components and/or devices, though the output is merely optional (e.g., control unit (1000) may merely be a diagnostic tool to receive information or the components and/or devices may be integrated with control unit (1000) such that control unit (1000) may directly activate or deactivate components and/or devices). In some versions, control unit (1000) further comprises EEPROM to store data thereon. For instance, the EEPROM may store machine readable code to control various components of surgical instrument (150) or the EEPROM may contain one or more operational settings and/or modes stored in data tables. Of course other machine readable code and/or configurations for the EEPROM will be apparent to one of ordinary skill in the art in view of the teachings herein. In some versions, control unit (1000) is integrated into generator (20) (shown in FIG. 1), though this is merely optional. In other versions control unit (1000) is integrated into surgical instrument (150) (such as control units (1000) shown in FIGS. 6-7) or control unit (1000) may be an independent device.

In the present example, transducer temperature sensor (190) transmits a signal that is indicative of the temperature of transducer (180) to control unit (1000). Control unit (1000) is configured to deactivate transducer (180) when a certain predetermined temperature is indicated by transducer temperature sensor (190). In some versions, control unit (1000) electrically decouples transducer (180) from generator (20) or electrically decouples transducer (180) from cable (30). Such electrical decoupling may be accomplished by an electrically controlled switch. Control unit (1000) may also be configured to audibly alert the user that the deactivation temperature has been reached or is about to be reached, though this is merely optional. A speaker (not shown) may be included on or within surgical instrument (150) to emit the auditory alert. Alternatively, a visual signal may be used (e.g., an indicator light or a pop-up alert on a display). Thus, transducer temperature sensor (190) and control unit (1000) may be used to monitor the temperature of transducer (180), deactivate transducer (180) if necessary, and/or provide alerts to the user. In some versions, sensor (190) may directly deactivate and/or decouple transducer (180), without switching being performed by/through control unit (1000), when the temperature of transducer (180) exceeds a threshold (e.g., when sensor (190) comprises a thermocouple/thermistor, etc.).

In addition or in the alternative, control unit (1000) and/or transducer temperature sensor (190) may be configured to continuously output the temperature signal for a user to observe or for another device to monitor and control surgical instrument (150). For instance, generator (20) and/or control unit (1000) may include a video screen (not shown) that displays the temperature signal output from transducer temperature sensor (190). The display of the temperature signal may be visual (such as a graph or a plurality of colored LEDs), numerical, or otherwise. In other versions, the video screen may be mounted to surgical instrument (150).

As noted earlier, trigger position sensor (192) is also communicatively coupled to control unit (1000). In the present example, the positional signal from trigger position sensor (192) is transmitted to control unit (1000) to monitor the position of trigger (168). In one version, control unit (1000) may maintain transducer (180) in a deactivated state until a certain position for trigger (168) is indicated by trigger position sensor (192). As similarly described earlier in reference to FIG. 1, trigger (168) controls a clamp arm (not shown) that clamps tissue against a blade (not shown). Thus, control unit (1000) may prevent the activation of transducer (180) until a certain position for trigger (168) is achieved. In a further version, control unit (1000) may be configured to deactivate transducer (180) if a certain predetermined position for trigger (168) is not maintained while transducer (180) is activated. If trigger position sensor (192) indicates that trigger (168) has been released, then control unit (1000) deactivates transducer (180). In a further variation, control unit (1000) may vary the power for transducer (180) depending upon the positional signal received from trigger position sensor (192). For instance, if trigger position sensor (192) indicates trigger (168) has not been actuated a large distance (such as if the user grasps a large amount of tissue), then control unit (1000) may be configured to activate transducer (180) at a first predetermined level. Alternatively, if trigger position sensor (192) indicates trigger (168) has been fully actuated or is substantially actuated (such as if the user grasps a small amount of tissue or no tissue at all), then control unit (1000) may be configured to activate transducer (180) at a second predetermined level. Of course the activation of transducer (180) is not limited to a first predetermined level or second predetermined level, but may be varied during the operation of surgical instrument (150).

It should be understood that the output of trigger position sensor (192) may be used in conjunction with the output of one or more other sensors such that control unit (1000) may provide appropriate control instructions and/or activation or deactivation instructions for various components of surgical instrument (150) based upon the various combinations of sensed conditions. By way of example only, strain gauge output (such as from strain gauge (286) of FIGS. 3A-3B) and/or force output (such as from yoke sensor (194) of FIG. 2, distal pad sensor (226), and/or proximal pad sensor (236) of FIGS. 3A-3B) may be transmitted to control unit (1000) and used to determine the amount, size, type, etc. of tissue clamped within the end effector. Some merely exemplary sensors, user input, and/or feedback that may be used with control unit (1000) is disclosed in U.S. patent application Ser. No. 13/151,481, entitled "Motor Driven Electrosurgical Device with Mechanical and Electrical Feedback," filed Jun. 2, 2011, published as U.S. Pat. Pub. No. 2012/0116379 on May 10, 2012, now U.S. Pat. No. 9,161,803, issued on Oct. 20, 2014, the disclosure of which is incorporated by reference herein.

In the present example, yoke sensor (194) outputs a force signal to control unit (1000) to indicate the force applied by yoke (172) to the inner tubular actuation member (and therefore the force on the clamp arm of the end effector). If yoke sensor (194) indicates a large force, yet trigger position sensor (192) indicates that trigger has not been actuated a large distance, then control unit (1000) is configured to determine that a large piece of tissue is clamped within the end effector. Accordingly, control unit (1000) activates transducer (180) at a first predetermined level to sever the tissue. Such activation may be automatic or in response to a selection by the user (e.g., a user pressing and holding a toggle button). If yoke sensor (194) indicates little or no force, yet trigger position sensor (192) indicates that trigger has not been actuated a large distance, then control unit (1000) is configured to determine that little or no tissue is clamped within the end effector. In response, control unit (1000) is operable to maintain transducer (180) in a deactivated state even if the user attempts to activate transducer (180). If yoke sensor (194) indicates little or no force and trigger position sensor (192) indicates that trigger has been fully or substantially actuated, then control unit (1000) is configured to determine that thin tissue or no tissue is clamped within the end effector. In response, control unit (1000) is operable to activate transducer (180) at a second predetermined level to sever the tissue. Such activation may be automatic or in response to a selection by the user (e.g., a user pressing and holding a toggle button). If yoke sensor (194) indicates a large force and trigger position sensor (192) indicates that trigger has been fully or substantially actuated, then control unit (1000) is configured to determine that a dense tissue is clamped within the end effector. In response, control unit (1000) is operable to activate transducer (180) at a third predetermined level to sever the dense tissue. Such activation may be automatic or in response to a selection by the user (e.g., a user pressing and holding a toggle button). Of course the foregoing system using control unit (1000), yoke sensor (194), and trigger position sensor (192) is merely exemplary and other configurations and/or outputs from control unit (1000) in response to the sensor inputs will be apparent to one of ordinary skill in the art in view of the teachings herein.

In addition or in the alternative, the output of trigger position sensor (192) may be used to activate one or more motors (not shown) to actuate components of surgical instrument (150) and/or other surgical instruments. One example of such a motorized surgical instrument will be shown and described in reference to FIG. 6.

It should be further understood that while the foregoing transducer temperature sensor (190), trigger position sensor (192), and yoke sensor (194) have been described in reference to an ultrasonic surgical instrument (150), transducer temperature sensor (190), trigger position sensor (192), and yoke sensor (194) may be incorporated into other surgical instruments, including endocutters, graspers, cutters, staplers, clip appliers, access devices, drug/gene therapy delivery devices, and energy delivery devices using RF, laser, etc.

B. Exemplary End Effector for Ultrasonic Surgical Instrument with Sensors

Figure 3A:
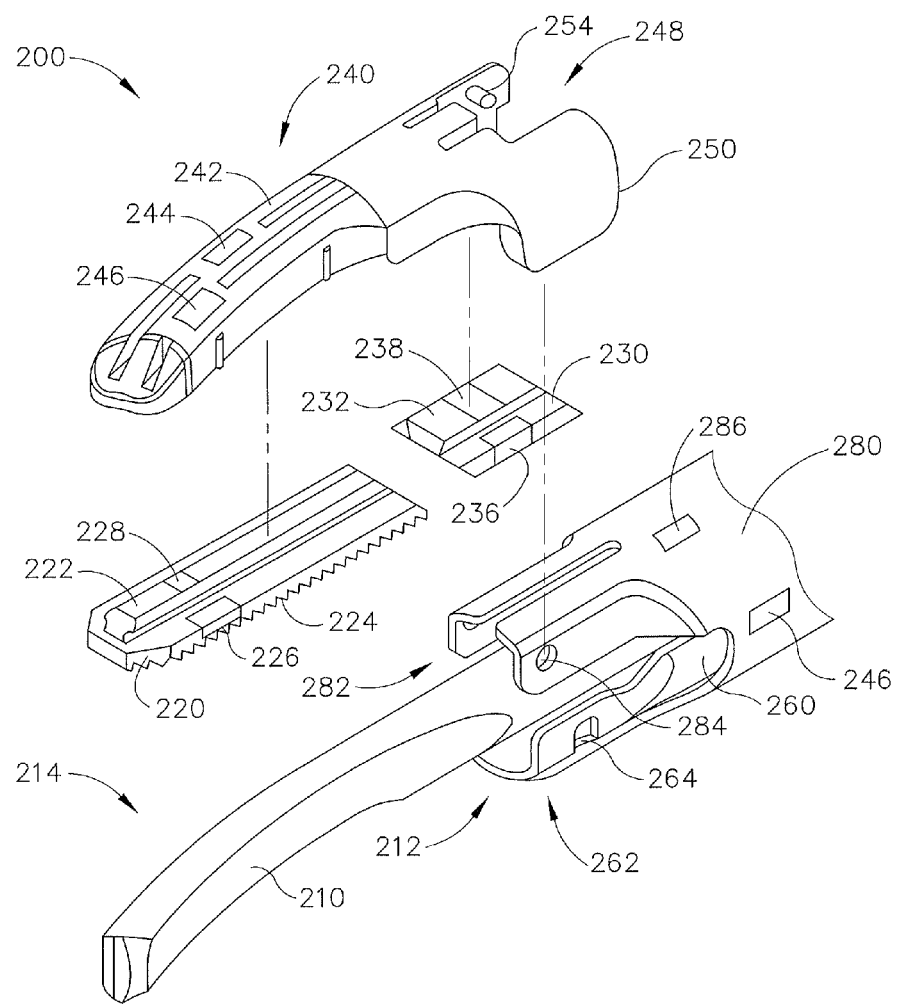
FIG. 3A depicts an exploded perspective view of an exemplary ultrasonic end effector having a plurality of sensors with the end effector shown in a closed position.
Figure 3B:
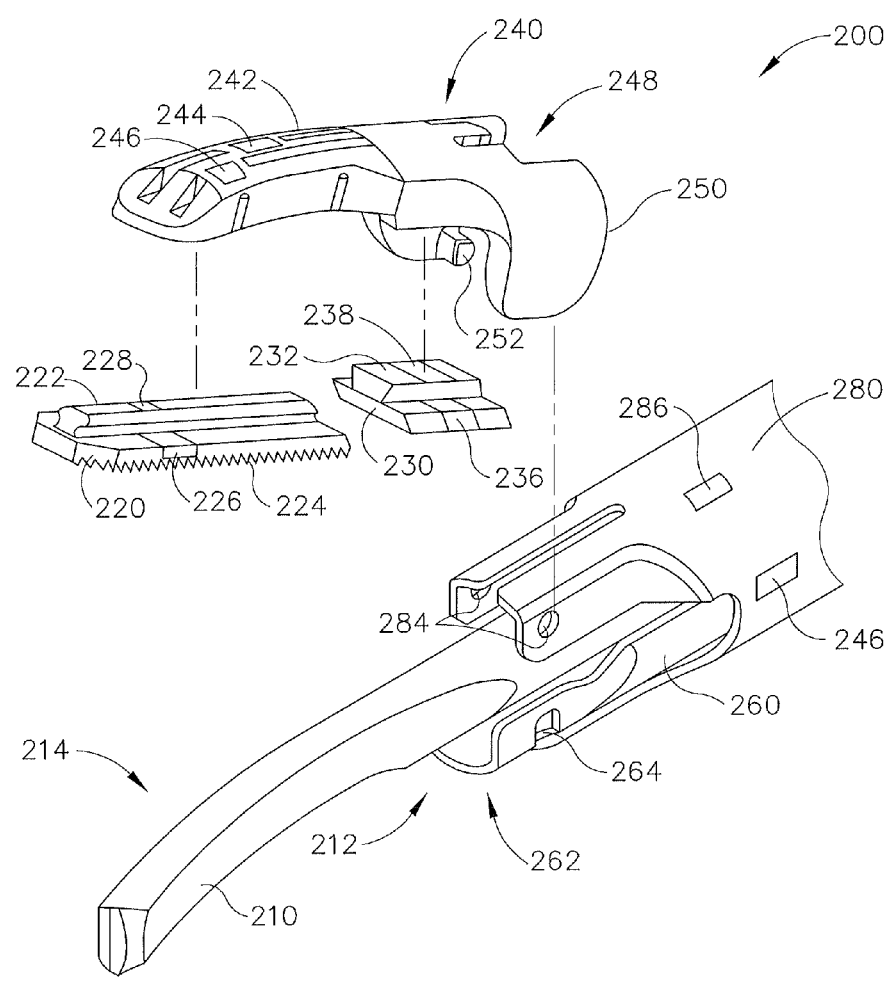
FIG. 3B depicts an exploded perspective view of the end effector of FIG. 3A shown in an open position.

FIGS. 3A-3B depict an exploded view of an exemplary end effector (200) shown in a closed position, FIG. 3A, and an open position, FIG. 3B. In the present example, end effector (200) comprises a blade (210), a distal clamp pad (220), a proximal clamp pad (230), and a clamp arm (240). An inner tubular actuation member (260) and an outer sheath (280) are components of a transmission assembly that extends distally from a handle assembly, such as transmission assembly (70) and handle assembly (60) described above. Blade (210) may be constructed in accordance with at least some of the teachings of blade (82) described above or in accordance with at least some of the teachings of U.S. Pat. Pub. No. 2006/0079874, now abandoned; U.S. Pat. Pub. No. 2007/0191713, now abandoned; U.S. Pat. Pub. No. 2007/0282333, now abandoned; U.S. Pat. Pub. No. 2008/0200940, now abandoned; U.S. Pat. Pub. No. 2011/0015660, issued as U.S. Pat. No. 8,461,744 on Jun. 11, 2013; and/or U.S. Pat. Pub. No. 2009/0143797, issued as U.S. Pat. No. 8,419,757 on Apr. 16, 2013, the disclosures of each are incorporated by reference herein. In the present example, blade (210) is configured to be coupled to a transducer, such as transducers (100, 180), and to oscillate at an ultrasonic frequency. Such a coupling of blade (210) to the transducer may be via a waveguide (not shown). When tissue is secured between blade (210) and clamp arm (240), the ultrasonic oscillation of blade (210) may simultaneously sever the tissue and denature the proteins in adjacent tissue cells, thereby providing a coagulative effect with relatively little thermal spread. An electrical current may also be provided through blade (210) and clamp arm (240) to cauterize the tissue. As shown, blade (210) comprises a cylindrical body portion (212) and a curved portion (214) at the distal end of blade (210). By way of example only, blade (210) comprises a solid titanium rod having a curved rectangular cuboid end. It should be understood that blade (210) may be substantially straight and/or blade (210) may have other geometries, including a conical end, a triangular prism end, a cylindrical end, a substantially planar end, a rectangular cuboid body, and/or any other geometry as will be apparent to one of ordinary skill in the art in view of the teachings herein. Further still, blade (210) may comprise materials other than titanium, including aluminium, steel, iron, composites, alloys, etc. Of course other configurations for blade (210) will be apparent to one of ordinary skill in the art in view of the teachings herein.

i. Exemplary Distal Clamp Pad with Sensor

Distal clamp pad (220) of the present example includes Teflon® (of E. I. du Pont de Nemours and Company of Wilmington, Del.), though other low-friction materials may be used as will be apparent to one of ordinary skill in the art in view of the teachings herein. Distal clamp pad (220) mounts on to clamp arm (240) via a T-shaped member (222) extending from distal clamp pad (220) and insertable into a T-shaped recess (not shown) of clamp arm (240). Distal clamp pad (220) is pivotable to a position that is substantially parallel to, and in contact with, blade (210). Accordingly, when clamp arm (240) is actuated to the closed position, shown in FIG. 3A, tissue is compressed and grasped between distal clamp pad (220) and blade (210). As illustrated, distal clamp pad (220) includes a non-smooth surface (224), such as a saw tooth-like configuration, to enhance the gripping of tissue by distal clamp pad (220). The saw tooth-like configuration, or teeth, provide traction against the movement of tissue relative to blade (210). As will be appreciated by one of ordinary skill in the art, the saw tooth-like configuration is just one example of many tissue engaging surfaces that may be used to prevent movement of the tissue relative to the movement of blade (210). Other illustrative examples include bumps, interlaced patterns, tread patterns, a bead or sand blasted surface, etc. In the example shown, distal clamp pad (220) is insertable into clamp arm (240) at a distal end and is disposed distally of proximal clamp pad (230).

Distal clamp pad (220) further comprises a distal clamp sensor (226). Distal clamp sensor (226) of the present example comprises a strain gauge or force sensitive resistor operable to determine the force exerted upon distal clamp pad (220) when clamp arm (240) is actuated to a closed position by trigger (168). The strain gauge or force sensitive resistor may be calibrated against a known standard prior to being coupled to distal clamp pad (220). Distal clamp sensor (226) is also communicatively coupled to control unit (1000). In the present example, a pad contact (228) is located on T-shaped member (222) to electrically couple to a complementary contact (not shown) on clamp arm (240). Accordingly, force signals representative of the force applied to distal clamp pad (220) may be communicated from distal clamp sensor (226) to control unit (1000). Thus, distal clamp sensor (226) may be used by control unit (1000) to determine the presence or absence of tissue between distal clamp pad (220) and blade (210). Furthermore, distal clamp sensor (226) may be used in conjunction with other sensors to determine the size and/or density of tissue as well. For instance, if distal clamp sensor (226) outputs a signal indicating a force is applied and inclinometer (246), described below, and/or yoke sensor (196) indicates that clamp arm (240) is not substantially actuated, control unit (1000) may be configured to determine that a large amount of tissue is present between clamp arm (240) and blade (210). Accordingly, control unit (1000) may output instructions to activate transducer (180), either automatically or when a toggle button is triggered by the user, at a first predetermined level. If distal clamp sensor (226) outputs a signal indicating a large force and inclinometer (246) and/or yoke sensor (196) indicates that clamp arm (240) is fully or substantially actuated, control unit (1000) may be configured to determine that a thin dense tissue is present between clamp arm (240) and blade (210). Accordingly, control unit (1000) may output instructions to activate transducer (180), either automatically or when a toggle button is triggered by the user, at a second predetermined level. If distal clamp sensor (226) outputs a signal indicating that a low force is applied and inclinometer (246) and/or yoke sensor (196) indicates that clamp arm (240) is fully or substantially actuated, control unit (1000) may be configured to determine that a thin, less dense tissue is present between clamp arm (240) and blade (210). Accordingly, control unit (1000) may output instructions to activate transducer (180), either automatically or when a toggle button is triggered by the user, at a third predetermined level. If distal clamp sensor (226) outputs a signal indicating that no force is applied, then control unit (1000) may be configured to deactivate transducer (180) or prevent the user from activating transducer (180). Of course other uses and/or configurations for distal clamp sensor (226) will be apparent to one of ordinary skill in the art in view of the teachings herein.

ii. Exemplary Proximal Clamp Pad with Sensor

Proximal clamp pad (230) comprises a substantially flat clamp pad that includes Teflon® (of E. I. du Pont de Nemours and Company of Wilmington, Del.), though other low-friction materials may be used as will be apparent to one of ordinary skill in the art in view of the teachings herein. Proximal clamp pad (230) mounts on to clamp arm (240) via a dove-tailed member (232) extending from proximal clamp pad (230) and insertable into a dove-tailed recess (not shown) of clamp arm (240). Proximal clamp pad (230) is also pivotable to a position that is substantially parallel to, and in contact with, blade (210). Accordingly, when clamp arm (240) is actuated to the closed position, shown in FIG. 3A, tissue is compressed between proximal clamp pad (230) and blade (210). Of course, since distal clamp pad (220) and proximal clamp pad (230) are distinct components, the material for distal clamp pad (220) and proximal clamp pad (230) may be different. Distal clamp pad (220) and/or proximal clamp pad (230) may be further constructed in accordance with at least some of the teachings of U.S. Pat. Pub. No. 2006/0079874, entitled "Tissue Pad for Use with an Ultrasonic Surgical Instrument," published Apr. 13, 2006, now abandoned, the disclosure of which is incorporated by reference herein.

Proximal clamp pad (230) further comprises a proximal clamp sensor (236). Proximal clamp sensor (236) of the present example comprises a strain gauge or a force sensitive resistor configured to determine the force exerted upon proximal clamp pad (230) when clamp arm (240) is actuated to a closed position by trigger (168). The strain gauge or force sensitive resistor may be calibrated against a known standard prior to being coupled to proximal clamp sensor (236). Proximal clamp sensor (236) is also communicatively coupled to control unit (1000). In the present example, a pad contact (238) is located on dove-tailed member (232) to electrically couple to a complementary contact (not shown) on clamp arm (240). Accordingly, force signals representative of the force applied to proximal clamp pad (230) may be communicated from proximal clamp sensor (236) to control unit (1000). Thus, proximal clamp sensor (236) may be used by control unit (1000) to determine the presence or absence of tissue between proximal clamp pad (230) and blade (210). Furthermore, proximal clamp sensor (236) may be used in conjunction with other sensors to determine the size and/or density of tissue as well. In some versions, control unit (1000) may be configured to prevent activation of transducer (180) if tissue is contained between proximal clamp pad (230) and blade (210), though this is merely optional. In addition or in the alternative, if distal clamp sensor (226) outputs a signal indicating the presence of tissue and proximal clamp sensor (236) does not output a signal indicating the presence of tissue, then control unit (1000) may be configured to activate transducer (180) at a first predetermined level. If both distal clamp sensor (226) and proximal clamp sensor (236) output a signal indicating the presence of tissue, then control unit (1000) may be configured to activate transducer (180) at a second predetermined level. Of course the foregoing is merely exemplary and more sensors or fewer sensors than distal clamp sensor (226) and proximal clamp sensor (236) may be used. Furthermore, control unit (1000) may have other configurations and/or settings in response to the various signals received from distal clamp sensor (226) and/or proximal clamp sensor (236). Of course other uses and/or configurations for proximal clamp sensor (236) will be apparent to one of ordinary skill in the art in view of the teachings herein.

iii. Exemplary Inner Tubular Actuation Member

Inner tubular actuation member (260) of the present example is a hollow cylindrical member configured to actuate longitudinally within outer sheath (280) while blade (210) extends longitudinally through inner tubular actuation member (260). The proximal end of inner tubular actuation member (260) is coupled to a trigger, such as triggers (68, 168), configured to actuate inner tubular actuation member (260) proximally when the trigger is depressed. When the trigger is released, inner tubular actuation member (260) actuates distally. Distal end (262) of inner tubular actuation member (260) comprises a pair of actuation holes (264) disposed on opposing sides of inner tubular actuation member (260) and configured to receive a pair of lower pins (252) of clamp arm (240). Accordingly, when clamp arm (240) is coupled to inner tubular actuation member (260) via actuation holes (264) and lower pins (252), the longitudinal motion of inner tubular actuation member (260) pivots clamp arm (240) about a pair of upper pins (254) of clamp arm (240). Of course other configurations and coupling mechanisms for inner tubular actuation member (260) will be apparent to one of ordinary skill in the art in view of the teachings herein. For instance, inner tubular actuation member (260) may include living hinges and be constructed in accordance with at least some of the teachings of U.S. patent application Ser. No. 13/274,830, entitled "Surgical Instrument with Modular Clamp Pad," filed Oct. 17, 2011, published as U.S. Pat. Pub. No. 2012/0116433 on May 10, 2012, now U.S. Pat. No. 9,192,428, issued on Nov. 24, 2015, the disclosure of which is incorporated by reference herein.

iv. Exemplary Outer Sheath with Sensor

Outer sheath (280) of the present example is also a hollow cylindrical member configured to couple to a casing of a handle assembly at a proximal end (not shown) of outer sheath (280) while blade (210), and inner tubular actuation member (260), and the waveguide associated with blade (210) extend longitudinally therethrough. Outer sheath (280) has a distal end (282) that includes a pair of upper holes (284) disposed on opposing sides of outer sheath (280) and configured to receive a pair of upper pins (254) of clamp arm (240). As will be apparent to one of ordinary skill in the art, upper holes (284) provide a pivot point about which clamp arm (240) is pivotable. Outer sheath (280) is further configured to be longitudinally fixed relative to inner tubular actuation member (260). Thus, when inner tubular actuation member (260) actuates longitudinally, outer sheath (280) provides a mechanical ground enabling clamp arm (240) to be pivoted. Of course, outer sheath (280) need not necessarily be fixed relative to inner tubular actuation member (260). By way of example only, inner tubular actuation member (260) may be fixed and outer sheath (280) may be actuatable or, in other versions, both inner tubular member (260) and outer sheath (280) may be actuatable. Of course other configurations for outer sheath (280) will be apparent to one of ordinary skill in the art in view of the teachings herein. For instance, outer sheath (280) may include living hinges and be constructed in accordance with at least some of the teachings of U.S. patent application Ser. No. 13/274,830, entitled "Surgical Instrument with Modular Clamp Pad," filed Oct. 17, 2011, published as U.S. Pat. Pub. No. 2012/0116433 on May 10, 2012, now U.S. Pat. No. 9,192,428, issued on Nov. 24, 2015, the disclosure of which is incorporated by reference herein.

In the present example, outer sheath (280) includes a strain gauge (286) mounted to a portion of outer sheath (280). Strain gauge (286) is communicatively coupled to control unit (1000) and is operable to measure the force on end effector (200) as applied to outer sheath (280). Strain gauge (286) may be calibrated against a known standard prior to being coupled to outer sheath (280). Strain gauge (286) shown in FIGS. 3A-3B measures the force applied to outer sheath (280) when clamp arm (240) is actuated to clamp tissue against blade (210). Accordingly, the force signal produced by strain gauge (286) may indicate the density and/or size of the tissue. For instance, if a dense tissue is present, then strain gauge (286) may produce a signal indicating a large force when clamp arm (240) is actuated closed. Alternatively, if a thin tissue or no tissue is present, then strain gauge (286) may produce a signal indicating a small or no force when clamp arm (240) is actuated closed. Accordingly, control unit (1000) may be configured to adjust the settings for transducer (180) and/or other components in response to the force signals transmitted from strain gauge (286). Of course the output signal from strain gauge (286) may be used by control unit (1000) with other sensor signals as well. Furthermore, while strain gauge (286) is shown on outer sheath (280), it should be understood that strain gauge (286) may be located elsewhere, including on inner tubular actuation member (260) or on clamp arm (240). Furthermore, a plurality of strain gauges (286) may be employed to measure multiple directions of forces and/or the locations of forces. Still further configurations for strain gauge (286) will be apparent to one of ordinary skill in the art in view of the teachings herein. Moreover, other sensors may be coupled to outer sheath (280) in conjunction with, or in the alternative to, strain gauge (286). For instance, thermocouples, thermistors, inclinometers, etc. may be positioned on outer sheath (280). One such additional sensor is an inclinometer (246), which will be described in more detail below.

v. Exemplary Clamp Arm with Sensors

Clamp arm (240) comprises an engagement portion (242) and an attachment portion (248) proximal of engagement portion (242). Engagement portion (242) of the present example comprises a curved member having a substantially flat bottom face that includes a T-shaped recess configured to receive T-shaped member (222) of distal clamp pad (220). T-shaped recess includes a complementary contact to electrically couple to pad contact (228) of distal pad sensor (226). Engagement portion (242) has a curvature that is substantially similar to that of blade (210) of the present example. Of course if blade (210) is straight, then engagement portion (242) may also be straight. Engagement portion (242) may further be configured to curve downwardly about the sides of blade (210) such that engagement portion (242) forms a trough into which tissue may be compressed and severed by blade (210). Attachment portion (248) comprises a body member (250), a pair of lower pins (252), and a pair of upper pins (254). Body member (250) comprises a dove-tailed recess (not shown) configured to receive dove-tailed member (232) of proximal clamp pad (230). Dove-tailed recess includes a complementary contact to electrically couple to pad contact (238) of proximal pad sensor (226). As discussed above, lower pins (252) are insertable into actuation holes (264) of inner tubular actuation member (260) and upper pins (254) are insertable into upper holes (284) of outer sheath (280). Accordingly, when pins (252, 254) are inserted into holes (264, 284), clamp arm (240) is coupled to outer sheath (280) and inner tubular actuation member (260), and clamp arm (240) is pivotable relative to blade (210). Of course other configurations for clamp arm (240) will be apparent to one of ordinary skill in the art in view of the teachings herein. In some versions, pins (252, 254) may be separate pins insertable through holes formed in body member (232). In some other versions, clamp arm (240) may include living hinges and be constructed in accordance with at least some of the teachings of U.S. patent application Ser. No. 13/274,830, entitled "Surgical Instrument with Modular Clamp Pad," filed Oct. 17, 2011, published as U.S. Pat. Pub. No. 2012/0116433 on May 10, 2012, now U.S. Pat. No. 9,192,428, issued on Nov. 24, 2015, the disclosure of which is incorporated by reference herein.

Clamp arm (240) of the present example further comprises a clamp arm sensor (244) and an inclinometer (246). Clamp arm sensor (244) of the present example comprises a thermocouple or a thermistor configured to determine the temperature of clamp arm (240). In the present example, clamp arm sensor (244) is mounted to the top surface of clamp arm (240), though it should be understood that other locations and/or orientations for clamp arm sensor (244) will be apparent to one of ordinary skill in the art in view of the teachings herein. Merely exemplary alternative locations include on the bottom of clamp arm (240), embedded in distal clamp pad (220), embedded in proximal clamp pad (230), on inner tubular actuation member (260), and/or on outer sheath (280). In some versions clamp arm sensor (244) is configured to have a positive temperature coefficient (PTC), while in others clamp arm sensor (244) is configured to have a negative temperature coefficient (NTC). Of course other configurations for clamp arm sensor (244) will be apparent to one of ordinary skill in the art in view of the teachings herein.

Clamp arm sensor (244) is also communicatively coupled to control unit (1000). In the present example, clamp arm sensor (244) transmits a signal that is representative of the temperature of clamp arm (240) to control unit (1000). Control unit (1000) may be configured to deactivate transducer (180) when a predetermined temperature sensor value is indicated by clamp arm sensor (244). For instance, control unit (1000) may be operable to decouple power to transducer (180) at generator (20) or decouple cable (30) from transducer (180). Control unit (1000) may also be configured to audibly and/or visually alert the user that the deactivation temperature has been reached or is about to be reached, as has been described in more detail above. Thus, clamp arm sensor (244) and control unit (1000) may be used to monitor the temperature of clamp arm (240) and, indirectly, the tissue surrounding clamp arm (240).

In addition or in the alternative, control unit (1000) and/or clamp arm sensor (244) may be configured to continuously output the temperature signal for a user to observe. For instance, generator (20) and/or control unit (1000) may include a video screen (not shown) that displays the temperature signal(s). The display of the temperature signal may be either visual (such as a graph or a plurality of colored LEDs), numerical, or otherwise. In other versions, the display may be mounted to or contained within surgical instrument (150). Thus, the user may be able to monitor the temperature of clamp arm (240) during a procedure.

Of course, while clamp arm sensor (244) has been described in reference to an ultrasonic end effector, clamp arm sensor (244) may be used with other surgical instruments and/or end effectors. For instance, endocutters, graspers, cutters, staplers, clip appliers, access devices, drug/gene therapy delivery devices, and energy delivery devices using RF, laser, etc. It should also be understood that clamp arm sensor (244) need not necessarily be a temperature measuring sensor, but instead may be any other kind of sensor. For instance, clamp arm sensor (244) may instead be a strain gauge, an inclinometer, an optical sensor, etc.

Clamp arm (240) also includes a longitudinally oriented first inclinometer (246) coupled to clamp arm (240) that is operable to measure the pitch of clamp arm (240) relative to a predetermined orientation (e.g., relative to a horizontal plane, relative to a vertical plane, relative to blade (210), etc.). First inclinometer (246) is also communicatively coupled to control unit (1000) such that the inclination signals produced by first inclinometer (246) are transmitted to control unit (1000). In some versions, inclinometer (246) may be used in conjunction with other sensors (such as trigger position sensor (192) and/or second inclinometer (246)) to determine the orientation of clamp arm (240) and/or blade (210). For instance, first inclinometer (246) may indicate the position of clamp arm (240) relative to a horizontal plane and trigger position sensor (192) may indicate the position of trigger (168). Accordingly, control unit (1000) may determine the orientation of clamp arm (240) and blade (210) relative to the horizontal plane (i.e., pitch) based upon the signals from first inclinometer (246) and trigger position sensor (192).

In addition or in the alternative, first inclinometer (246) may indicate the orientation of clamp arm (240) relative to the horizontal plane and a second inclinometer (246) positioned on outer sheath (280), and perpendicularly oriented relative to first inclinometer (246), may also indicate the roll orientation of outer sheath (280) relative to the horizontal plane. Accordingly, with first inclinometer (246) and second inclinometer (246) communicatively coupled to control unit (1000), control unit (1000) may determine the orientation of clamp arm (240) and/or blade (210) relative to two planes (i.e., pitch and roll orientation).

In yet another alternative or in addition to the above, a solid state compass (not shown) may be included with surgical instrument (for example, in the handle assembly, in or on outer sheath (280), etc.) and configured to indicate the bearing of outer sheath (280). Accordingly, with first inclinometer (246), second inclinometer (246), and the solid state compass communicatively coupled to control unit (1000), control unit (1000) may determine the orientation of clamp arm (240) and/or blade (210) relative to three planes (i.e., pitch, roll, and yaw). In yet a further configuration, a GPS receiver and/or other positional electronics may be integrated into the surgical instrument. With such positional and/or orientation information, control unit (1000) may indicate on a display whether clamp arm (240) and/or blade (210) are oriented for optimum cutting of the tissue. For instance, a surgical path may be modeled prior to (or contemporaneously with) the surgery and control unit (1000) may provide feedback to the user regarding whether the severing of tissue is substantially in accordance with the modeled surgical path. Alternatively, such orientation feedback may be used in robotic surgery settings. Of course still other configurations and/or uses for inclinometers (246) will be apparent to one of ordinary skill in the art in view of the teachings herein.

While a merely exemplary end effector (200) has been described herein, other end effectors may be used as well. For instance, one or more of clamp arm (240), distal clamp pad (220), proximal clamp pad (230), inner tubular actuation member (260), and/or outer sheath (280) may be omitted from end effector (200). One merely exemplary end effector omitting proximal clamp pad (230), inner tubular actuation member (260), and outer sheath (280) is described in U.S. Pat. Pub. No. 2007/0191713, entitled "Ultrasonic Device for Cutting and Coagulating," published Aug. 16, 2007, now abandoned, the disclosure of which is herein incorporated by reference. Another merely exemplary end effector omitting clamp arm (240), distal clamp pad (220), proximal clamp pad (230), and inner tubular actuation member (260) is described in U.S. Pat. Pub. No. 2008/0200940, entitled "Ultrasonic Device for Cutting and Coagulating," published Aug. 21, 2008, now abandoned, the disclosure of which is herein incorporated by reference. Still other configurations for end effector (200) will be apparent to one of ordinary skill in the art in view of the teachings herein.

II. Overview of Exemplary Radiofrequency (RF) Surgical Instrument

Figure 4:
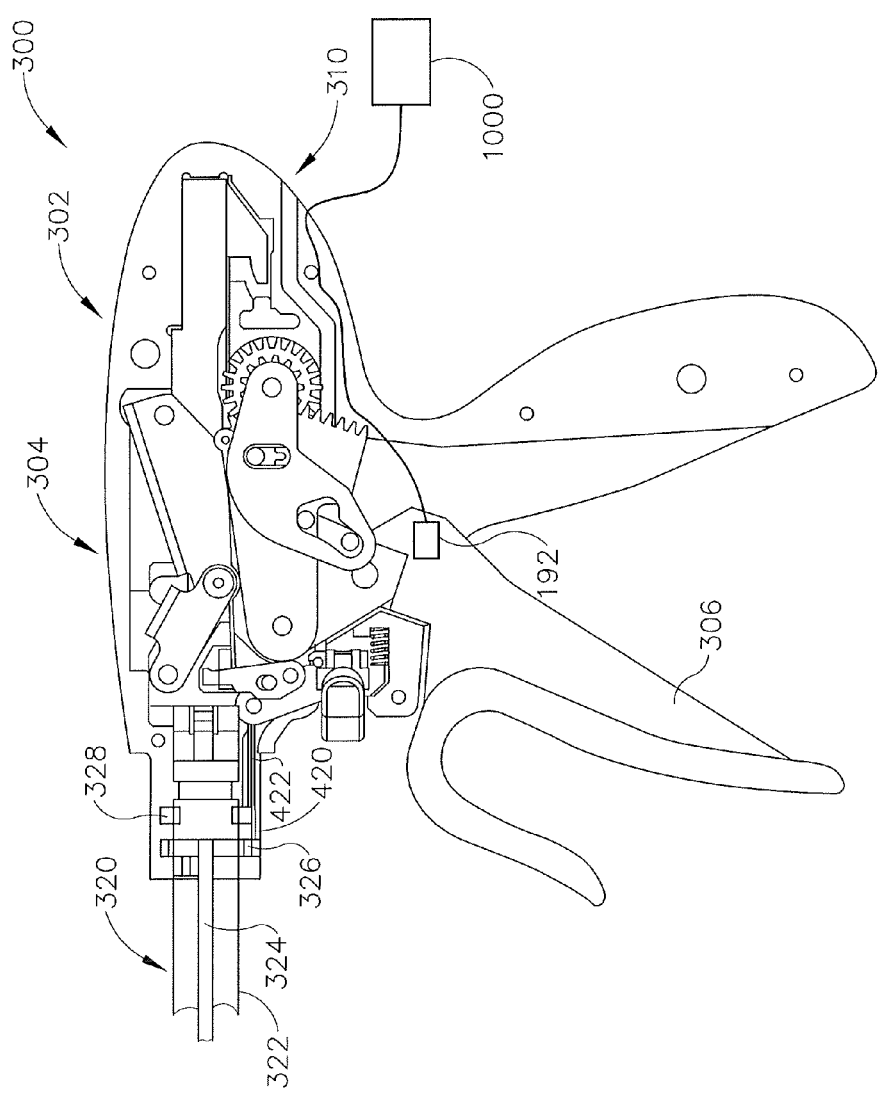
FIG. 4 depicts a side cross-sectional view of a handle assembly of an exemplary RF surgical instrument having a trigger position sensor coupled to a control unit.
Figure 5:
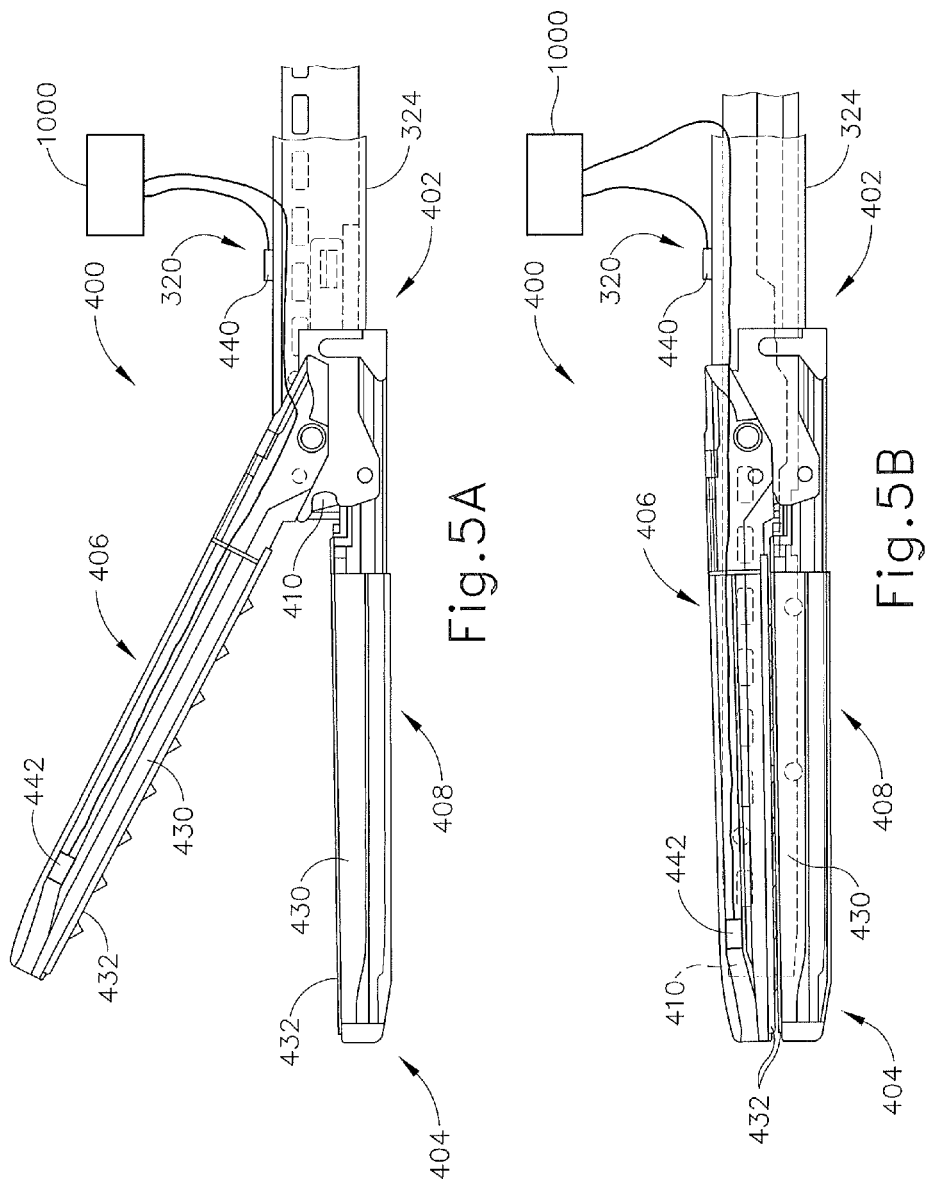
FIG. 5A depicts a side elevation view of an exemplary RF end effector having a plurality of sensors with the end effector shown in an open position.
FIG. 5B depicts a side elevation view of the end effector of FIG. 5A shown in a closed position.

While some surgical instruments are adapted to use ultrasonic energy to operate on tissue, other surgical instruments, such as surgical instrument (300), shown in FIGS. 4-5B, can be configured to supply energy, such as electrical energy and/or heat energy, to the tissue of a patient. Surgical instrument (300) includes a handle assembly (302), a transmission assembly (320), and an end effector (400) (shown in FIGS. 5A-5B) coupled to a distal end of transmission assembly (320). As described in greater detail below, handle assembly (302) may include one or more switches and/or triggers to supply electrical energy to end effector (400) and/or advance a knife or cutting member (410) (also shown in FIGS. 5A-5B) within end effector (400) to transect the tissue positioned within end effector (400).

A. Exemplary Handle Assembly with Sensors

Referring back to FIG. 4, handle assembly (302) comprises one or more electrical inputs (310) that are operably coupled with a power supply (not shown), such as generator (20) and/or any other power supply, including, for example, a power supply contained within handle assembly (302). A transmission assembly (320) extends distally from handle assembly (302) and includes end effector (400) coupled to a distal end of transmission assembly (320). The power supply provides an electrical current to surgical instrument (300), and the power supply may be operable to control the magnitude, duration, wave form, and/or frequency, of the current to provide a desired amount of energy to surgical instrument (300). Handle assembly (302) of the present example comprises a handle body (304) that is configured to support a switch or trigger (306) to selectively electrically couple electrical input (310) with a first conductor (420) extending through transmission assembly (320) such that the current supplied to input (310) can be transmitted to end effector (400). Trigger (306) of the present example also includes trigger position sensor (192) that produces and transmits signals to control unit (1000) indicating the position of trigger (306) relative to handle body (304). Trigger position sensor (192) may be further constructed and/or configured in accordance with the description of trigger position sensor (192) regarding FIG. 2 above. Handle body (304) comprises two longitudinally halved portions that are assembled together to form handle body (304). As depicted in FIG. 4, one portion has been omitted to show some of the various internal components of handle assembly (302). In various embodiments, the halves of handle body (304) can be snap-fit, press-fit, welded, adhered together, and/or fastened to one another as will be apparent to one of ordinary skill in the art in view of the teachings herein. Further still, handle assembly (302) may be a unitary piece instead of two discrete halves. In yet another alternative, the portions may not be halves, but merely discrete coupleable components, such as a handle body (304) with a removable top and/or side portion. Still other configurations for handle body (304) will be apparent to one of ordinary skill in the art in view of the teachings herein.

First conductor (420) comprises a wire, such as insulated wire, that extends between trigger (306) and a first electrode (430), shown in FIGS. 5A-5B in end effector (400), and also between trigger (306) and input (310). In the present example, first conductor (420) is coupled to a first electrode (430) in an upper jaw (406) and a first electrode (430) in a lower jaw (408), though it should be understood that first electrode (430) may be in only upper jaw (406) or in only lower jaw (408). A first slip ring (326) electrically couples a portion of first conductor (420) extending through transmission assembly (320) to a portion of first conductor (320) contained within handle assembly (302). Handle assembly (302) further comprises a second conductor (422) that is also electrically coupled to the power supply via input (310) and extends through transmission assembly (320) to end effector (400) to a second electrode (432). In the present example, second conductor (422) is coupled to second electrode (432) in upper jaw (406) and second electrode (432) in lower jaw (408), though it should be understood that second electrode (432) may be in only upper jaw (406) or in only lower jaw (408). Transmission assembly (320) comprises an outer sheath (322) that is coaxial to, and disposed about, a shaft (324) such that shaft (324) is contained within outer sheath (322). Second conductor (422) comprises a wire with an insulative plastic jacket or sheath to insulate second conductor (422) relative to first conductor (420), shaft (324), and/or first electrode (430). A second slip ring (328) is configured to electrically couple a portion of second conductor (422) extending through transmission assembly (320) to a portion of second conductor (422) contained within handle assembly (302). Slip rings (326, 328) of the present example each comprise a circular, or an at least semi-circular, contact that is mounted within handle body (304) and which remains in contact with a corresponding circular, or an at least semi-circular, contact mounted to a portion of transmission assembly (320). Slip rings (326, 328) thus permit rotation of transmission assembly (320) relative to handle assembly (302) while still providing an electrical path for first and second conductors (420, 422) through transmission assembly (320).

Of course handle assembly (302) and surgical instrument (300) may include other configurations. For instance, handle assembly (302) and/or surgical instrument (300) may include a tissue cutting element and one or more elements that transmit bipolar RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201, entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued on Jan. 27, 2015, the disclosure of which is incorporated by reference herein; and U.S. patent application Ser. No. 13/151,481, entitled "Motor Driven Electrosurgical Device with Mechanical and Electrical Feedback," filed Jun. 2, 2011, published as U.S. Pat. Pub. No. 2012/0116379 on May 10, 2012, now U.S. Pat. No. 9,161,803, issued on Oct. 20, 2014, the disclosure of which is incorporated by reference herein.

B. Exemplary RF End Effector

End effector (400) of the present example comprises an upper jaw (406) and a lower jaw (408). Upper jaw (406) is pivotable relative to lower jaw (408) and is operable to clamp tissue between upper jaw (406) and lower jaw (408) via actuation of shaft (324). Actuation of shaft (324) may be accomplished via actuation of trigger (306), by a second trigger, by a button, by a motor, by a solenoid, and/or by any other suitable method. Both upper jaw (406) and lower jaw (408) of the present example include first electrode (430) which extends between a proximal end (402) and a distal end (404) of end effector (400), shown in FIGS. 5A-5B. First electrode (430) of the present example comprises a first lateral portion extending along a first side of both upper jaw (406) and lower jaw (408), a second lateral portion extending along a second side of both upper jaw (406) and lower jaw (408), and a transverse end portion connecting the first lateral portion and the second lateral portion for both upper jaw (406) and lower jaw (408), thereby forming a U-shaped longitudinal electrode in both upper jaw (406) and lower jaw (408). Upper jaw (406) and lower jaw (408) of the present example further comprise second electrode (432) of a similar shape as first electrode (430), but insulated from first electrode (430) and inset from first electrode (430). In some instances, upper jaw (406) includes only first electrode (430) and lower jaw (408) includes only second electrode (432), or vice versa. In still another configuration, second electrode (432) may be actuatable with cutting member (410). Both upper jaw (406) and lower jaw (408) include a longitudinal channel (not shown) configured to permit cutting member (410) to translate longitudinally therein. Still other configurations for end effector (400) are disclosed in U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pat. Pub. No. 2011/0087218, now U.S. Pat. No. 8,939,974, issued on Jan. 27, 2015; and/or U.S. patent application Ser. No. 13/151,481, entitled "Motor Driven Electrosurgical Device with Mechanical and Electrical Feedback," filed Jun. 2, 2011, published as U.S. Pat. Pub. No. 2012/0116379 on May 10, 2012, now U.S. Pat. No. 9,161,803, issued on Oct. 20, 2014, the disclosures of which are incorporated by reference herein.

Still referring to FIGS. 5A-5B, end effector (400) of the present example further comprises an upper jaw sensor (442) and an inclinometer (440). Upper jaw sensor (442) of the present example comprises a thermocouple or a thermistor configured to determine the temperature of upper jaw (406). In the present example, upper jaw sensor (442) is mounted to upper jaw (406), though it should be understood that other locations and/or orientations for upper jaw sensor (442) will be apparent to one of ordinary skill in the art in view of the teachings herein. Merely exemplary alternative locations include lower jaw (408), shaft (324), and/or outer sheath (322). In some versions upper jaw sensor (442) is configured to have a positive temperature coefficient (PTC), while in others upper jaw sensor (442) is configured to have a negative temperature coefficient (NTC). Of course other configurations for upper jaw sensor (442) will be apparent to one of ordinary skill in the art in view of the teachings herein.

Upper jaw sensor (442) is also communicatively coupled to control unit (1000). In the present example, upper jaw sensor (442) transmits a signal that is representative of the temperature of upper jaw (406) to control unit (1000). Control unit (1000) may be configured to deactivate surgical instrument (300) when a certain temperature is indicated by upper jaw sensor (442). Control unit (1000) may also be configured to audibly alert the user that the deactivation temperature has been reached or is about to be reached. Thus, upper jaw sensor (442) and control unit (1000) may be used to monitor the temperature of upper jaw (406) and control surgical instrument (300) accordingly.

In addition or in the alternative, control unit (1000) and/or upper jaw sensor (442) may be configured to continuously output the temperature signal for a user to observe. For instance, a generator, such as generator (20), and/or control unit (1000) may include a video screen (not shown) that displays the temperature signal(s). The display of the temperature signal may be either visual (such as a graph or a plurality of colored LEDs), numerical, or otherwise. In other versions, the display may be mounted to or contained within surgical instrument (150). Thus, the user may be able to monitor the temperature of upper jaw (406) during a procedure.

Of course, while upper jaw sensor (442) has been described in reference to an RF end effector, upper jaw sensor (442) may be used with other surgical instruments and/or end effectors. For instance, endocutters, graspers, cutters, staplers, clip appliers, access devices, drug/gene therapy delivery devices, and energy delivery devices using ultrasonic, laser, etc. It should also be understood that upper jaw sensor (442) need not necessarily be a temperature measuring sensor, but instead may be any other kind of sensor mounted to upper jaw (406). For instance, upper jaw sensor (442) may instead be a strain gauge, an inclinometer, an optical sensor, etc.

Inclinometer (440) of the present example is mounted to shaft (324) and is proximal of cutting member (410). Similar to inclinometers (246) shown and described in relation to FIGS. 3A-3B, inclinometer (440) is configured to measure the pitch of shaft (324) relative to a predetermined orientation (e.g., relative to a horizontal plane, relative to a vertical plane, etc.). Inclinometer (440) is also communicatively coupled to control unit (1000) such that the signals produced by inclinometer (440) are transmitted to control unit (1000) to indicate the inclination of shaft (324) relative to the predetermined orientation. Such orientation information may be used to ensure an optimum angle for cutting through the tissue prior to the closure of upper jaw (406) against lower jaw (408) and actuation of cutting member (410). In some versions, inclinometer (440) may be used in conjunction with other sensors (such as trigger position sensor (192), a second inclinometer (440) mounted to upper jaw (406), a solid state compass, GPS receiver, and/or other positional sensor) to determine the orientation of cutting member (410) and/or upper jaw (406).

In the present example, trigger (306) (shown in FIG. 4) is operable to both clamp tissue between upper jaw (406) and lower jaw (408) and to selectively supply energy from the power supply to first electrode (430) via first conductor (420). Second electrode (432) may remain constantly coupled to the power supply via second conductor (422) when power supply is coupled to electrical input (310) or, in some versions, a second trigger and/or button may selectively supply power to second electrode (432). Accordingly, when trigger (306) is actuated, current flows from first electrode (430) to second electrode (432) to cauterize the tissue therebetween. This heat may denature the collagen within the tissue and, in co-operation with clamping pressure provided by jaws (406, 408) of end effector (400), the denatured collagen may form a seal within the tissue. In some versions, trigger (306) provides an indication to the generator to provide current to the electrodes. Thus, in such versions, trigger (306) is not simply a switch in line with the current flow that is operable to selectively break the current flow.

Upper jaw sensor (442) of the present example is used to monitor the temperature produced at end effector (400) when current is flowing between first electrode (430) and second electrode (432). In some versions upper jaw sensor (442) may be used to monitor a minimum temperature and a maximum temperature to determine when the tissue is adequately sealed, but not overheated. While the present exemplary end effector (400) is configured to use bipolar RF energy to seal the tissue, it should be understood that other versions may use monopolar RF energy and/or other thermal heating elements. The first lateral side of electrodes (430, 432) is configured to create a first lateral seal within the tissue and the second lateral side of electrodes (430, 432) is configured to create a second lateral seal within the tissue. Of course other configurations may include multiple electrodes, and/or multiple electrode portions, that can create any suitable number of seals in any orientation within the tissue. With the tissue sealed on either end of the longitudinal channels of upper jaw (406) and lower jaw (408), cutting member (410) is actuated distally to sever the two laterally sealed portions of tissue. The active RF energy may assist with such severing (in addition to sealing the tissue). Cutting member (410) may be actuated by a second trigger (not shown) or, in one alternative version, by further actuation of trigger (306). In the present example, cutting member (410) comprises an upper flange and a lower flange on opposing ends of a blade, thereby forming an I-shaped member. As cutting member (410) is actuated distally, the flanges assist in compressing upper jaw (406) against lower jaw (408).

Of course end effector (400) and/or surgical instrument (300) may include other configurations as will be apparent to one of ordinary skill in the art in view of the teachings herein.

III. Exemplary Alternative Handle Assembly with Force and Position Sensors

In some instances the user may desire feedback while they are using a surgical instrument. For instance, the force required to advance cutting member (410) may be important if sensitive tissue is being severed by surgical instrument (300). In addition, the speed at which cutting member (410) is advanced through the tissue may also be important to a user. Accordingly, the ability to monitor and provide feedback to the user about the force and speed of cutting member (410) and/or shaft (326) may be desirable to some users. In alternative devices, the force applied to an inner tubular actuation member (260) may correspond to the clamping force applied by a clamp arm (240). Accordingly, the ability to monitor the force on the inner tubular actuation member (260) may permit the user to monitor the clamping force on the tissue. Furthermore, the ability to visually indicate the relative values of the force and/or speed measurements may also be desirable to a user such that the user may alter their use of the device. Accordingly, the following example describes one such exemplary handle assembly. It should be understood that the following description may be applied to a variety of surgical instruments and is not intended to be limited to the device and/or end effector described herein.

Figure 6:
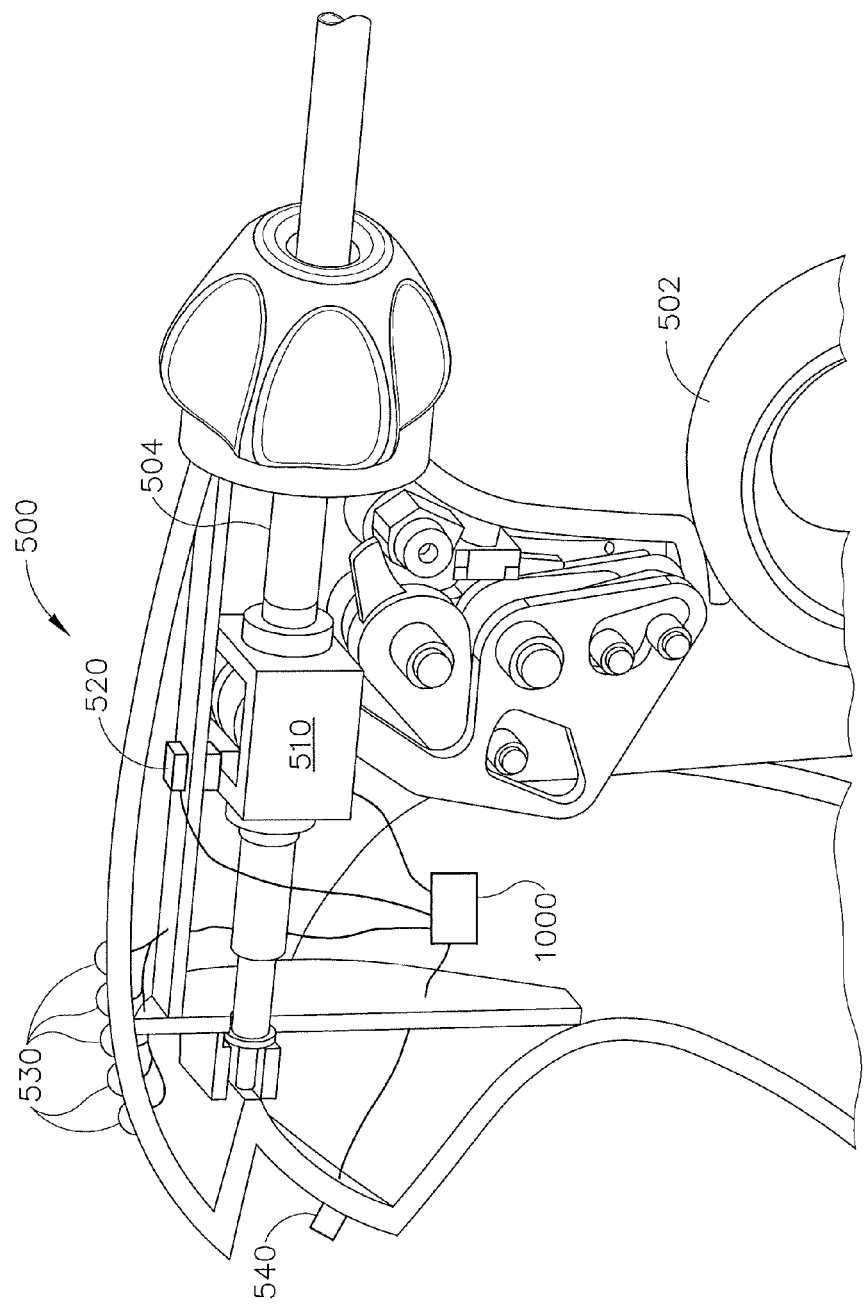
FIG. 6 depicts a perspective view of an exemplary handle assembly having a force sensor and a position sensor therein.

FIG. 6 depicts an alternative handle assembly (500) comprising a force sensor (510) and a position sensor (520). In the present example, some components of handle assembly (500) have been omitted for clarity, but it should be understood that handle assembly (500) may be constructed in accordance with at least some of the teachings of handle assemblies (302, 160, 60) described herein and/or in accordance with at least some of the teachings of U.S. Pat. No. 6,500,176; U.S. Pat. No. 6,783,524; U.S. Pat. No. 7,416,101; U.S. Pat. No. 7,738,971; U.S. Pat. No. 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0209990, issued as U.S. Pat. No. 8,657,174 on Feb. 25, 2014; U.S. Pub. No. 2009/0043797, now abandoned; U.S. Pub. No. 2010/0069940, now U.S. Pat. No. 9,023,071, issued on May 5, 2015; and/or U.S. Provisional Application Ser. No. 61/410,603. As shown in FIG. 6, handle assembly (500) includes a trigger (502) that is coupled to a shaft (504) and also to force sensor (510). Trigger (502) is operable to actuate shaft (504) longitudinally relative to handle assembly (500). Shaft (504) may be constructed in accordance with at least some of the teachings for shaft (324) shown in FIGS. 4-5B or, in some versions, shaft (504) may be constructed in accordance with at least some of the teachings of inner tubular actuation member (260) shown in FIGS. 3A-3B. Force sensor (510) is coupled to trigger (502) and shaft (504) and is configured to measure the force transmitted from trigger (502) to shaft (504). In the present example, force sensor (510) comprises a force transducer, though other force measurement sensors may be used as will be apparent to one of ordinary skill in the art in view of the teachings herein. Force sensor (510) is communicatively coupled to control unit (1000) and is operable to transmit signals indicating the force applied to shaft (504).

Position sensor (520) is coupled to shaft (504) and is configured to measure the longitudinal displacement of shaft (504) relative to an initial predetermined position. In the present example, position sensor (520) comprises a linear potentiometer, though it should be understood that other positional sensors may be used (e.g., linear encoders, linearly arranged optical sensors, etc.). By way of example only, the initial predetermined position may correspond to the position of shaft (504) prior to actuation by trigger (502). Accordingly, when trigger (502) is actuated by a user, shaft (504) is longitudinally actuated and position sensor (520) measures the longitudinal displacement of shaft (504). Position sensor (520) is also communicatively coupled to control unit (1000) and is operable to transmit signals indicating the linear displacement of shaft (504).

Control unit (1000) of the present example is located within handle assembly (500), though this is merely optional. Indeed, as discussed previously, control unit (1000) may be integrated into a generator, such as generator (20), or control unit (1000) may be a separate device. In the present example, control unit (1000) is configured to receive the force measurements from force sensor (510) and the positional measurements from position sensor (510). With these measurements, control unit (1000) is configured to determine the force applied to shaft (324) and the advancement speed of shaft (324). Control unit (1000) may be further configured to compare the foregoing values against predetermined force and/or advancement speed values. Control unit (1000) may then determine whether too much, too little, or an appropriate amount of force is being applied to the tissue. In addition, control unit (1000) may also determine whether shaft (324) is distally advancing too fast, too slow, or at an appropriate speed. In some versions, such as in robotic surgical settings, control unit (1000) may be adapted to output adjusted control signals in response to the relative force and/or speed determinations to actuators and/or other components configured to operate the surgical instrument. In other versions, such as where a user is operating the surgical instrument, sensory indicators may be provided to give feedback to a user. Merely exemplary sensory feedback may be in the form of visual, auditory, tactile, etc.

In the present example, a plurality of indicators (530) are mounted to handle assembly (500) and are coupled to control unit (1000) such that control unit (1000) is operable to manipulate indicators (530). Indicators (530) of the present example comprise a plurality of LEDs, though other indicators may be used. Merely exemplary alternative indicators (530) include a dynamic graphical display, auditory sounds, a force feedback mechanism coupled to trigger (502), etc. As shown in FIG. 6, five indicators (530) are coupled to control unit (1000). Of course any number of indicators (530) may be used, including 1, 2, 3, 4, 6, 7, or more. In this example, the central indicator (530) corresponds to an output from control unit (1000) that indicates that an appropriate speed and/or force is being applied to shaft (324). Distal indicators (530) indicate outputs from control unit (1000) corresponding to predetermined values indicating shaft (324) is advancing too fast and/or that the force applied to shaft (324) is too high. Proximal indicators (530) indicate outputs from control unit (1000) corresponding to two different predetermined values indicating shaft (324) is advancing too slow and/or that the force applied to shaft (324) is too low. Alternatively, indicators (530) may have various colors such that the different colors correspond to positive and/or negative feedback. Of course other configurations for control unit (1000) and/or indicators (530) will be apparent to one of ordinary skill in the art in view of the teachings herein.

In some versions, multiple sets of indicators (530) may indicate multiple different outputs from control unit (1000). For instance, one set of indicators (530) may indicate the relative speed of shaft (324) (too fast/too slow/adequate) as determined by control unit (1000) while a second set of indicators (530) may indicate the relative force on shaft (324) (too high/too low/adequate) as determined by control unit (1000). Such sets of indicators (530) may be arranged as parallel lines of LEDs. In some alternative versions, the two sets of indicators (530) may be arranged perpendicular to each other (such as in an L shape, T shape, or in a cross). Still further arrangements for indicators (530) will be apparent to one of ordinary skill in the art in view of the teachings herein.

The present example further includes a toggle switch (540) communicatively coupled to control unit (1000). Toggle switch (540) of the present example includes a plurality of positions corresponding to a plurality of predetermined settings. By way of example only, toggle switch (540) may be configured to adjust control unit (1000) for different types of tissue (e.g., thick soft tissue, thick hard tissue, thin hard tissue, thin soft tissue, etc.), though it should be understood that other configurations for toggle switch (540) and/or control unit (1000) may be used. For instance, toggle switch (540) may include a plurality of positions corresponding to a plurality of predetermined settings for various types of end effectors, shaft lengths, etc. In response to movement of toggle switch (540), control unit (1000) of the present example is configured to use a corresponding table of predetermined values of forces and/or positions for the selected tissue type. Accordingly, a user may select the appropriate values for control unit (1000) using toggle switch (540) prior to using the surgical instrument. Once the user begins to use surgical instrument, control unit (1000) receives the signals from force sensor (510) and position sensor (520) and compares the values to the predetermined values selected by toggle switch (540). Control unit (1000) then outputs the appropriate signals to indicators (530) to indicate whether the user is advancing shaft at the appropriate speed and/or with the appropriate force. Accordingly, the user may adjust their use of the surgical instrument according to the indications provided by indicators (530). Of course toggle switch (540) is merely optional and may be omitted.

In some settings, the feedback provided by indicators (530) may be used to train users of the surgical instrument prior to use on a living person or organism. For instance, medical students may use a surgical instrument having indicators (530) to practice with the surgical instrument prior to first using the device on a living person or organism. Alternatively, such feedback may be used by the user to indicate optimal use of the surgical instrument to achieve hemostasis. Further still, the feedback may be used (either by the user or by control unit (1000)) to monitor the use of the surgical instrument to prevent damage due to improper use. Still further configurations and/or uses for handle assembly (500) will be apparent to one of ordinary skill in the art in view of the teachings herein.

IV. Exemplary Handle Assembly Having Motors

In some settings, a user may prefer to have mechanical assistance or motorized components. Such control may permit a variety of users having a variety of physical characteristics to control the surgical instrument in substantially the same manner. For instance, some users may have more or less hand strength than other users. Moreover, in some settings, the motorized control may permit the user to operate the surgical instrument remotely. Furthermore, such motorized control may permit control unit (1000) to control the order in which certain actions are performed (e.g., clamping the tissue prior to activating transducer (100, 180), sealing the tissue prior to advancing a cutting member (410), stapling the tissue prior to advancing a cutting member (410), etc.). Accordingly, the following describes various constructions for handle assemblies that implement motors and/or motor assistance for various components of the handle assemblies.

A. Handle Assembly Having a Motor Driven Blade Shaft and Clamp Shaft

Figure 7:
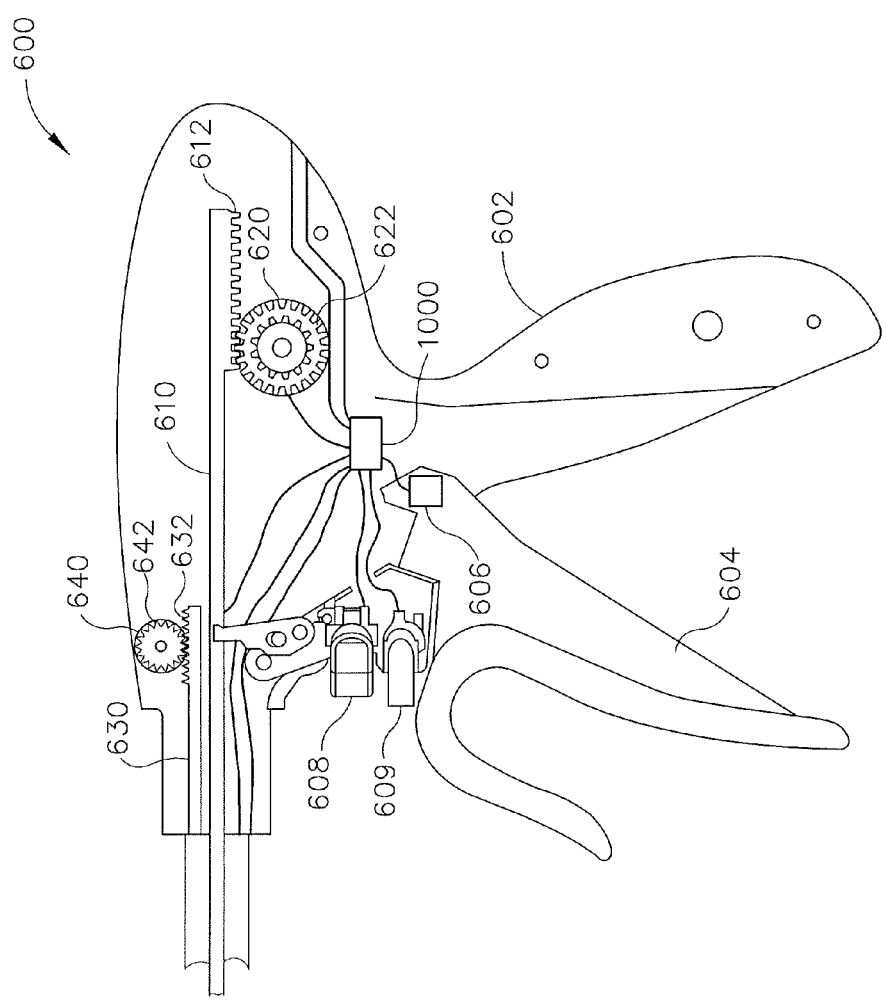
FIG. 7 depicts a side elevation view of an exemplary handle assembly having a pair of motors therein.

FIG. 7 depicts an exemplary handle assembly (600) having a casing (602), a trigger (604) pivotable relative to casing (602), a trigger position sensor (606), a pair of toggle buttons (608, 609), a longitudinally actuatable blade shaft (610), a first motor (620), an actuatable clamp shaft (630), and a second motor (640). Trigger (604) of the present example is pivotable from a first, open position (shown in FIG. 7) to a second, closed position (not shown). As shown in FIG. 7, trigger (604) is pivotably coupled to trigger position sensor (606), though it should be understood that this is merely optional. Accordingly, it should be understood that trigger (604) does not engage any other components of handle assembly (600) other than trigger position sensor (606) and casing (602). Thus, the force required by a user to rotate trigger (604) may be substantially reduced to only the frictional resistance from trigger position sensor (606) and/or casing (602). Of course, a spring or other resiliently member may be provided to bias trigger (604) to the open position. In some versions, a feedback mechanism, such as a motor or a linear actuator (not shown), may be coupled to trigger (604) to provide force-feedback to trigger (604). In other versions trigger (604) may be pivotably coupled to casing (602) or omitted entirely (e.g., in a robotically controlled surgical instrument or a remotely operated device). Such a remotely operated device with optional force-feedback mechanisms will be described in greater detail below.

Trigger position sensor (606) of the present example is coupled to casing (602) and trigger (604) and is operable to measure the rotational displacement of trigger (604) relative to a first predetermined position, such as the open position shown in FIG. 7. Trigger position sensor (606) may comprise a potentiometer, an encoder, an optical sensor, and/or any other rotational and/or positional measurement sensor as will be apparent to one of ordinary skill in the art in view of the teachings herein. Trigger position sensor (606) is also communicatively coupled to control unit (1000) such that the signals produced by trigger position sensor (606) are transmittable to control unit (1000). While control unit (1000) of the present example is shown within handle assembly (600), it should be understood that control unit (1000) may be integrated into a power supply, such as generator (20) of FIG. 1, or control unit (1000) may be an independent device.

First motor (620) is operable to longitudinally advance blade shaft (610) relative to casing (602). In the present example, motor (620) comprises a rotational motor having a pinion gear (622) operable to engage and actuate a rack (612) on blade shaft (610). Blade shaft (610) of the present example is coupled to an end effector and is operable to advance a cutting member to sever tissue clamped within the end effector. In some versions, blade shaft (610) may be operable to both clamp the end effector and sever tissue, such as in cutting member (410) of end effector (400) shown in FIGS. 5A-5B. Alternatively, blade shaft (610) may be coupled to other components of an end effector, such as to clamp arm (240) of end effector (200) shown in FIG. 3A-3B. Still other configurations for blade shaft (610) will be apparent to one of ordinary skill in the art in view of the teachings herein. In some versions, a gearbox (not shown) may be provided between rack (612) of blade shaft (610) and gear (622) on motor (620) to alter the gear ratio either up or down. Motor (620) may comprise a servo motor, a piezoelectric motor, a stepper motor, a brushed motor, a brushless motor, a pancake motor, and/or any other motor as will be apparent to one of ordinary skill in the art in view of the teachings herein. In some other versions, motor (620) may be omitted and a linear actuator, a pneumatic cylinder, a piezoelectric actuator, a hydraulic cylinder, and/or any other actuation device may be coupled to blade shaft (610) to provide movement to blade shaft (610). Motor (620) of the present example is also communicatively coupled to control unit (1000) and is operable to receive output control signals from control unit (1000). Still further configurations for motor (620) and/or blade shaft (610) will be apparent to one of ordinary skill in the art in view of the teachings herein.

Second motor (640) of the present example is operable to longitudinally advance clamp shaft (630) relative to casing (602). In the present example, motor (640) comprises a rotational motor having a pinion gear (642) operable to engage a rack (632) on clamp shaft (630). Clamp shaft (630) of the present example is coupled to an upper jaw of the end effector, and clamp shaft (630) is operable to pivot the upper jaw to clamp tissue against a lower jaw (not shown). The end effector, upper jaw, and/or lower jaw may be constructed in accordance with at least some of the teachings of end effector (400), upper jaw (406), and/or lower jaw (408) described above. It should be understood that clamp shaft (630) may be coupled to other components and/or end effectors as will be apparent to one of ordinary skill in the art in view of the teachings herein. In some versions, a gearbox (not shown) may be provided between rack (632) of clamp shaft (630) and gear (642) of motor (640) to alter the gear ratio either up or down. Motor (640) may comprise a servo, a piezoelectric motor, a stepper motor, a brushed motor, a brushless motor, a pancake motor, and/or any other rotary motor as will be apparent to one of ordinary skill in the art in view of the teachings herein. In some versions, motor (640) may be omitted and a linear actuator, a pneumatic cylinder, a piezoelectric actuator, a hydraulic cylinder, and/or any other linear actuation device may be coupled to clamp shaft (630) to provide linear movement. Motor (640) of the present example is also communicatively coupled to control unit (1000) and motor (640) is operable to receive output control signals from control unit (1000). Still further configurations for motor (640) and/or clamp shaft (630) will be apparent to one of ordinary skill in the art in view of the teachings herein.

Toggle buttons (608, 609) are communicatively coupled to control unit (1000) and are configured to activate one or more functional aspects of the surgical instrument. In the present example, first toggle button (608) is configured to activate the RF components of an end effector, such as first electrode (230) and second electrode (232) described above, to coagulate or seal the tissue clamped by the end effector. In addition or in the alternative, first toggle button (608) may activate second motor (640) to advance clamp shaft (630) described above. Further still, in other surgical instruments, first toggle button (608) may actuate a sled to drive staples out of a staple cartridge. In yet another configuration, first toggle button (608) may activate an ultrasonic transducer. Of course still further configurations and operable uses for first toggle button (608) will be apparent to one of ordinary skill in the art in view of the teachings herein. Second toggle button (609) of the present example is configured to activate first motor (620) to distally advance blade shaft (610). Other features of the surgical instrument may be activated by second toggle button (609) as will be apparent to one of ordinary skill in the art in view of the teachings herein.

Control unit (1000) of the present example is operable to receive input from toggle buttons (608, 609) and trigger position sensor (606) and to output control signals to first motor (620) and/or second motor (640). Control unit (1000) is further configured to activate the RF components of the end effector coupled to handle assembly (600), though it should be understood that control unit (1000) is not limited to use with RF end effectors. Furthermore, it should be understood that toggle buttons (608, 609), trigger (604), and trigger position sensor (606) are merely optional and may be omitted. Indeed, as will be described below, a remote device may be used to transmit the appropriate input signals to control unit (1000) to control first motor (620), second motor (640) and any additional components to use the end effector coupled to handle assembly (600).

In the present example, control unit (1000) is operable to activate and control second motor (640) in response to the pivoting of trigger (604) by a user. Control unit (1000) receives the output from trigger position sensor (606) and outputs control signals to second motor (640). Accordingly, as the user rotates trigger (604), trigger position sensor (606) transmits the position signals to control unit (1000). Control unit (1000) then transmits a corresponding output signal to second motor (640) such that second motor (640) actuates clamp shaft (630) a predetermined distance corresponding to the rotation of trigger (604). By way of example only, control unit (1000) may output a pulse-width modulation signal to a servo motor to rotate the servo motor to a desired position. Of course other outputs and/or motor combinations will be apparent to one of ordinary skill in the art in view of the teachings herein. Since the user does not directly apply a force to actuate clamp shaft (630), users of varying strengths may rotate trigger (604) while motor (640) provides the force to actuate clamp arm shaft (630). In some versions, trigger (606) may be omitted and a remote device, such as a joystick, may be used to provide the input for control unit (1000) as will be described in more detail below. In addition or in the alternative, a computer program and/or instructions may provide the input values for control unit (1000) to operate second motor (640). Of course other configurations for second motor (640) and control unit (1000) will be apparent to one of ordinary skill in the art in view of the teachings herein.

Control unit (1000) is further operable to activate one or more components of the end effector in response to a user activating first toggle button (608). As noted previously, control unit (1000) may activate RF components of the end effector, such as first electrode (230) and second electrode (232) described above, to coagulate the tissue clamped within the end effector. Of course control unit (1000) may activate other components of other end effectors in response to a user's activation of first toggle button (608).

In the present example, control unit (1000) is also operable to output control signals to first motor (620) such that the actuation of blade shaft (610) may be controlled via control unit (1000). By way of example only, control unit (1000) may output a pulse-width modulation signal to a servo motor to rotate the servo motor to a desired position. Of course other outputs and/or motor combinations will be apparent to one of ordinary skill in the art in view of the teachings herein. In the present example, second toggle button (609) is configured to initiate control unit (1000) to activate second motor (620), thereby advancing blade shaft (610) and severing the tissue clamped and sealed within the end effector.

While the foregoing description details some basic functionalities of control unit (1000) for controlling and actuating various components of the surgical instrument having handle assembly (600), control unit (1000) may also be used to control the sequencing and timing of the actions of clamping, coagulating, and cutting performed by the end effector. It should be understood that the foregoing actions of clamping, coagulating, and cutting are merely exemplary and other actions may be controlled by control unit (1000) as well, such as activating an ultrasonic transducer, driving staples out of a staple cartridge, etc.

In the present example, when a user desires to clamp, coagulate, and sever tissue with the end effector coupled to handle assembly (600), initially the user positions the tissue between the upper jaw and lower jaw of the end effector. The user then initiates the clamping of tissue by actuating trigger (604). As described above, trigger (604) is pivotably coupled to trigger position sensor (606). Trigger position sensor (606) transmits a signal to control unit (1000) indicating the rotational position of trigger (604). In response to the new position signal transmitted by trigger position sensor (604), control unit (1000) activates second motor (640) to actuate clamp shaft (630) to the desired position. When trigger (604) is in the open position, as shown in FIG. 7, control unit (1000) is configured to provide control signals to second motor (640) such that the clamp arm or upper jaw of end effector is in the open position (such as those shown in FIGS. 3B and 5A). As the user rotates trigger (604) to the closed position, control unit (1000) provides control signals to second motor (640) to actuate clamp shaft (630) such that clamp arm or upper jaw of end effector rotates towards the closed position (such as those shown in FIGS. 3A and 5B). Of course, as noted above, trigger (604) is merely optional and other sources for input signals to control unit (1000) may be used instead of trigger (604) and trigger position sensor (606) of handle assembly (600).

Once trigger position sensor (606) indicates that trigger (604) has been pivoted to the closed position, the user may activate the end effector. In the present example, the user activates first toggle button (608), thereby instructing control unit (1000) to activate the RF components of the end effector. Of course other end effectors with other components may be activated by first toggle button (608). In some versions, control unit (1000) may disable first toggle button (608) until trigger position sensor (606) indicates that trigger (604) is pivoted to the closed position. Such disablement of first toggle button (608) may prevent a user from inadvertently activating the components of the end effector prior to clamping the tissue within the end effector. Once trigger position sensor (606) indicates that trigger (604) is pivoted to the closed position, control unit (1000) may enable first toggle button (608) to permit the user to activate first toggle button (608). As noted previously, the activation of first toggle button (608) causes control unit (1000) to activate the RF components of the end effector. In other versions, control unit (1000) may automatically activate the RF components of the end effector upon trigger position sensor (606) indicating that trigger (604) is pivoted to the closed position. In some versions, control unit (1000) may also instruct second motor (640) to dwell at the closed position until prompted by control unit (1000) to return to the open position. Such dwelling may maintain end effector in the closed position during the clamping, coagulating, and cutting of tissue even if the user releases trigger (604). Of course other configurations and controls for first toggle button (608) and control unit (1000) will be apparent to one of ordinary skill in the art in view of the teachings herein.

In the present example, control unit (1000) is coupled to one or more sensors to monitor the temperature of the tissue. For instance, the end effector may include an upper jaw sensor (442), described above, to monitor the temperature of the end effector (and indirectly the tissue nearby). Of course other sensors may be integrated into the end effector to monitor the coagulation of the tissue. In some alternative versions, control unit (1000) may be configured to prevent any other actions until a predetermined dwell time is reached. Such a dwell time may be used to permit adequate coagulation of the tissue by the end effector. Once the predetermined time has elapsed and/or the one or more sensors indicate that the tissue is adequately coagulated, control unit (1000) is configured to deactivate the RF components of the end effector and permit advancement of blade shaft (610) such that a cutting member may sever the tissue clamped by end effector. In the present example, control unit (1000) prevents blade shaft (610) from actuating until the tissue is adequately coagulated and sealed. In some versions, control unit (1000) may automatically output control instructions to first motor (620) to actuate blade shaft (610) once the tissue is adequately coagulated and sealed. In other versions, control unit (1000) may wait until the user instructs control unit (1000) to actuate blade shaft (610), such as via a user's activation of second toggle button (609). Once the user activates second toggle button (609), control unit (1000) instructs first motor (620) to advance blade shaft (610), thereby severing the tissue within the end effector.

With the tissue severed, control unit (1000) may automatically retract blade shaft (610) and actuate clamp shaft (630) to open the end effector to release the coagulated and severed tissue. In some versions, control unit (1000) may wait until the user pivots trigger (604) to the open position before blade shaft (610) is retracted and the end effector is opened. Of course various portions of the foregoing steps for clamping, coagulating, and severing tissue may be omitted and/or combined with various other portions described herein. By way of example only, the coagulating, severing, and releasing of tissue may all be performed automatically and in sequence by control unit (1000) once the user pivots trigger (604) to the closed position. Thus, the user may only need to perform one action—pivoting trigger (604) to the closed position—to initiate the surgical instrument to clamp, coagulate, and sever the tissue. Such automatic action may provide a more uniform pattern of coagulated and severed of tissue. In another version, control unit (1000) may wait for user input at each stage (e.g., after clamping, coagulating, and severing the tissue). Of course other configurations and sequences will be apparent to one of ordinary skill in the art in view of the teachings herein.

In some surgical instruments that both clamp and sever tissue utilizing the same actuation shaft (such as end effector (400) shown in FIGS. 5A-5B), control unit (1000) may actuate the shaft a short distance using motor (620) to initially clamp the tissue within the end effector. The tissue is then coagulated either upon initialization by the user activating first toggle button (608) or automatically by control unit (1000). Once the tissue is sufficiently coagulated, control unit (1000) then further advances the shaft to sever the tissue within the end effector. Still further configurations for control unit (1000) will be apparent to one of ordinary skill in the art in view of the teachings herein. Moreover, it should be understood that control unit (1000) may be utilized with non-motorized surgical instruments. By way of example only, control unit (1000) may control a locking feature that prevents the user from advancing blade shaft (610) prior to an indication that the tissue is adequately coagulated. As noted earlier, such an indication may be provided via one or more sensors or accordingly to a predetermined dwell time. Of course such locking features may also be provided for other manually activated portions of other surgical devices.

Further still, control unit (1000) may monitor the time and usage of the surgical instrument to provide diagnostic information about the surgical instrument and/or the end effector to prevent over usage of the surgical instrument and/or end effector. For example, for surgical instruments with a transducer, control unit (1000) may monitor the number of activations, the duration that the transducer is activated, and the overall time to determine whether the transducer may overheat. In reference to the present example, control unit (1000) may monitor the number of activations, the duration that the RF components are activated, and the overall time to determine whether the end effector may exceed predetermined temperature values.

B. Exemplary Remote Controller with Force-feedback and Adjustable Settings

Figure 8:
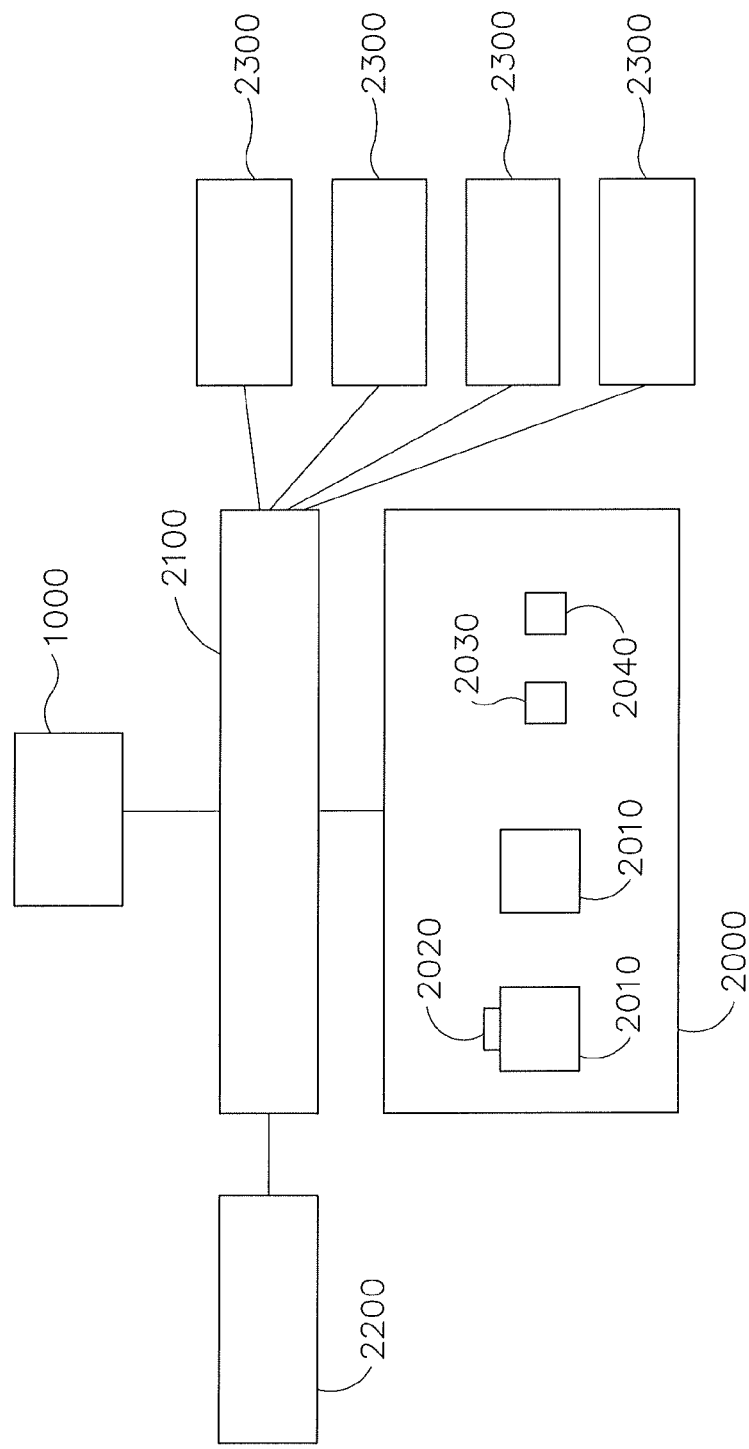
FIG. 8 depicts a diagrammatic view of an exemplary remote controller, surgeon interface, device interface, and additional input devices.

As mentioned previously, in some versions trigger (604), trigger position sensor (606), and toggle buttons (608, 609) may be omitted and a remote controller (2000), shown in FIG. 8, may be used to provide the desired inputs to control unit (1000). Remote controller (2000) is communicatively coupled to control unit (1000) via a wired connection or via a wireless connection such that commands from remote controller (2000) are transmittable to control unit (1000). In some versions, feedback is transmittable from control unit (1000) to remote controller (2000) to indicate one or more conditions of the surgical instrument. Remote controller (2000) may comprise one or more joysticks, one or more directional pads, one or more triggers, one or more buttons, and/or any other suitable input device for a user. By way of example only, remote controller (2000) shown in FIG. 8 includes a pair of joysticks (2010), a clamp trigger (2020), an end effector activation button (2030), and a blade actuation button (2040). The pair of joysticks (2010) may be configured to output instructions to control unit (1000) to control the depth, rotation, vertical position, horizontal position, pitch, and/or yaw of the end effector and/or handle assembly (600) via one or more motors operable to adjust the position and/or orientation of handle assembly (600). Clamp trigger (2020) includes a sensor configured to sense the rotational position of clamp trigger (2020) in substantially the same manner as trigger position sensor (606). Accordingly, when a user pivots clamp trigger (2020), remote controller (2000) transmits instructions to control unit (1000) to the clamp of the end effector to close. In the example of handle assembly (600), control unit (1000) instructs second motor (640) to rotate and translate clamp shaft (630) proximally or distally. End effector activation button (2030) and blade actuation button (2040) provide input signals in substantially the same manner as toggle buttons (608, 609) of the previously described example. Accordingly, when a user activates end effector activation button (2030), remote controller (2000) transmits instructions to control unit (1000) to activate one or more components of the end effector. Merely exemplary components that may be activated include RF components to coagulate and seal tissue, a transducer to oscillate a blade to sever tissue, a shaft to translate a sled to drive staples out of a cartridge, and/or any other component of an end effector. When a user activates blade actuation button (2040), remote controller (2000) transmits instructions to control unit (1000) to advance a cutting member (such as cutting member (410)) to sever tissue clamped within the end effector. Accordingly, a user may control the surgical instrument and/or end effector remotely through the use of remote controller (2000).

In the present example, a device interface (2100) is interposed between remote controller (2000) and control unit (1000). Device interface (2100) comprises an integrated circuit or a microcontroller configured to interface with control unit (1000), remote controller (2000), a surgeon interface (2200), and one or more device inputs (2300). In the present example, device interface (2100) is configured to receive inputs from surgeon interface (2200), one or more additional input devices (2300), and control unit (1000) about the conditions of the tissue, operating parameters, surgeon preference, etc. Surgeon interface (2200) of the present example comprises an integrated circuit or a microcontroller configured to receive inputs from a user and output the desired settings to device interface (2100). By way of example only, surgeon interface (2200) may include a physical user interface (E.g., toggle buttons, switches, etc.) or surgeon interface (2200) may comprise a software user interface (e.g., software having a plurality of settings that are adjustable by the user). Merely exemplary output from surgeon interface (2200) may include the tissue type, the tissue size, the tissue thickness, the operating conditions, the maximum or minimum end effector temperature, the maximum or minimum clamping force, usage time maximum, suction irrigation settings, energy levels for a transducer, cutting or coagulating modes, and/or any other output as will be apparent to one of ordinary skill in the art in view of the teachings herein. Thus, a surgeon may provide a variety of settings as input for device interface (2100) based upon the user's experience and judgment. Using this input, device interface (2100) is further configured to adjust the control instructions from remote controller (2000) in response to the collective conditions and settings. For instance, for soft tissue, device interface (2100) may limit or decrease the clamping force and advancement speed of the cutting member even if the user provides contradictory instructions while using remote controller (2000). In another example, for hard, thick tissue, device interface (2100) may increase the clamping force to ensure the end effector adequately grasps the tissue. Of course further configurations for surgeon interface (2200) and/or device interface (2100) will be apparent to one of ordinary skill in the art in view of the teachings herein.

In the present example, one or more additional input devices (2300) are communicatively coupled to device interface (2100) to provide input. Such additional input devices (2300) may provide input concerning the conditions of the tissue and/or other operating parameters. By way of example only, such additional input devices (2300) may include image processing devices, endoscopic systems, external and/or internal sensors for the surgical instrument, input devices for surgical assistants to input additional information, etc. Accordingly, device interface (2100) may also utilize these additional inputs to modify the control instructions from remote controller (2000) or, in some alternatives, to confirm the inputs received from surgeon interface (2200). Device interface (2100) then outputs the adjusted control instructions to control unit (1000). In some versions the output from device interface (2100) may be reduced to one or more table references such that control unit (1000) modifies one or more aspects of the surgical device according to a predetermined instruction table stored on control unit (1000) in a machine readable non-transitory medium (e.g., a data table of settings stored on EEPROM of control unit (1000)). Of course other additional input devices (2300) may be used with device interface (2100) to provide additional input.

In some versions, device interface (2100) may also receive sensor input from control unit (1000) and output instructions to force-feedback components of remote controller (2000) such that the pair of joysticks (2010) and/or clamp trigger (2020) provide tactile feedback to the user. By way of example only, one or more sensors may be coupled to handle assembly (600) to monitor the forces encountered by the end effector and/or other components of the surgical instrument. Merely exemplary sensors that may be used with the surgical instrument include, but are not limited to, yoke sensor (194) and strain gauge (286) described above. Such sensors may provide feedback to control unit (1000) to be transmitted to one or more force-feedback components of remote controller (2000). Such force-feedback components for remote controller (2000) may include one or more actuation devices, such as motors, linear actuations, etc., to provide a resistive force to the user's movement of the controls of remote controller (2000). These resistive forces are based upon the forces encountered by the end effector and/or other components of the surgical instrument. Alternatively, or in addition to the force-feedback, control unit (1000) may be configured to transmit a haptic feedback signal to device interface (2100) to activate the one or more actuation devices of remote controller (2000) momentarily. Such haptic feedback may indicate the completion of a certain step (e.g., completion of tissue coagulation or completion of the severing of tissue). Alternatively, remote controller (2000) may be further configured to provide visual, auditory, tactile, and/or other sensory feedback to indicate one or more sequence steps have been completed by completed by control unit (1000). Merely exemplary completed steps for which remote controller (2000) may provide sensory feedback include the adequate coagulation of tissue, a completely closed end effector clamping tissue, and/or a complete distal actuation of a cutting member to sever the tissue. Of course further configurations for control unit (1000) and/or remote controller (2000) will be apparent to one of ordinary skill in the art in view of the teachings herein.

C. Exemplary Adaptive Trigger Control

In some instances, a user may prefer to have variable control and/or feedback when actuating the trigger of a surgical device. For instance, if the clamping motion and/or the cutting member encounters a difficult item midway through the clamping and/or cutting motion, a user may prefer to stop clamping and/or cutting and possibly unclamp the end effector and/or retract the cutter. Accordingly, it may be preferable to have adaptive control over the motorized handle assembly.

Figure 9:
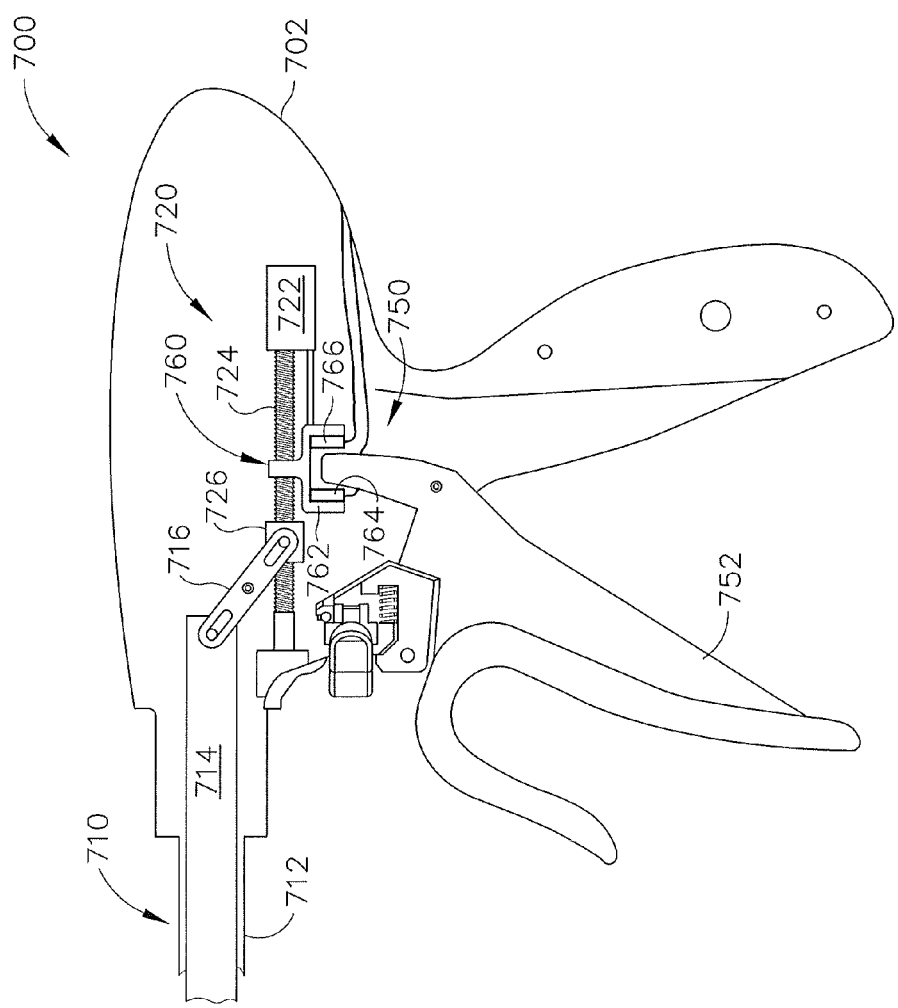
FIG. 9 depicts a side elevation view of an exemplary handle assembly having an adaptive trigger assembly.

FIG. 9 depicts an exemplary handle assembly (700) having an adaptive trigger assembly (750). In the present example, handle assembly (700) comprises a casing (702), a transmission assembly (710) extending distally from the casing (702), and a motor assembly (720). Transmission assembly (710) of the present example comprises an outer sheath (712) and an actuation member (714) longitudinally actuatable within the outer sheath (712). An end effector (not shown) is coupled to the distal end of the outer sheath (712) and actuation member (714). Actuation member (714) is operable to actuate one or more components in the end effector. For instance, if end effector (200) of FIGS. 3A-3B is coupled to the distal end of transmission assembly (710), actuation member (714) is operable to pivot clamp arm (240). Alternatively, if end effector (400) is coupled to the distal end of transmission assembly (710), actuation member (714) is operable to distally advance cutting member (410) to both clamp upper jaw (406) against lower jaw (408) and to sever tissue. Still other configurations for end effectors and actuation member (714) will be apparent to one of ordinary skill in the art in view of the teachings herein.

Actuation member (714) is coupled to a transfer member (716). Transfer member (716) comprises a linkage pivotably coupled at a first end to actuation member (714) and pivotably coupled at a second end to carriage member (726) of motor assembly (720). Transfer member (716) is also pivotably coupled to casing (704) at a midpoint. Accordingly, when carriage member (726) is advanced distally or proximally, transfer member (716) actuates actuation member (714) proximally or distally (opposite the direction of motion of carriage member (726)).

Motor assembly (720) comprises a motor (722), a screw gear (724) coupled to motor (722), and carriage member (726). Motor (722) is mounted within casing (702) and is operable to rotate screw gear (724). Screw gear (724) extends longitudinally within casing (702) and substantially parallel to the axis of actuation member (714). In the present example, carriage member (726) comprises internal threading that complements the threading of screw gear (724), and carriage member (726) is carried on screw gear (724). As will be apparent to one of ordinary skill in the art in view of the teachings herein, when motor (722) rotates screw gear (724), carriage member (726)—being rotationally limited by the coupling to transfer member (716)—translates relative to casing (702). Accordingly, motor (722) is operable to actuate actuation member (714) via carriage member (726) and transfer member (714). In the present example, resistor carriage (760), described in more detail below, is also carried by screw gear (724) and translatable via rotation of screw gear (724) by motor (722), though this is merely optional.

Trigger assembly (750) comprises trigger (752) pivotably mounted to casing (702) and resistor carriage (760). Resistor carriage (760) of the present example comprises a body (762), a distal force sensitive resistor (764), and a proximal force sensitive resistor (766). In the present example, distal force sensitive resistor (764) and proximal force sensitive resistor (766) are configured such that when a force is applied to either distal force sensitive resistor (764) or proximal force sensitive resistor (766), then the resistance is decreased. Accordingly, the more force applied to trigger (752) in the corresponding direction by the user, then the lower the resistance in distal force sensitive resistor (764) or proximal force sensitive resistor (766). In the present example, when trigger (752) is pivoted toward the closed position, trigger (752) contacts distal force sensitive resistor (764), thereby reducing the resistance of distal force sensitive resistor (764). When trigger (752) is pivoted toward the open position, trigger (752) contacts proximal force sensitive resistor (766), thereby reducing the resistance of proximal force sensitive resistor (766). When no force is applied to trigger (752), trigger (752) does not exert any force on either distal force sensitive resistor (764) or proximal force sensitive resistor (766). Thus, when a power source (not shown) is electrically coupled to distal force sensitive resistor (764), proximal force sensitive resistor (766), and motor (720), actuation of trigger (752) by the user causes motor (722) to rotate screw gear (724) proximally or distally.

As noted earlier, resistor carriage (760) is carried by screw gear (724) such that resistor carriage (760) actuates as trigger (752) is pivoted. Accordingly, the motion of trigger (752) is linked to the motion of actuation member (714). The harder the user pulls the trigger (752), the faster motor (722) runs and the faster resistor carriage (760) translates on screw gear (724). In some versions, trigger (752) may be resiliently biased toward the open position. Accordingly, if the user releases trigger (752), trigger (752) is configured to contact proximal force sensitive resistor to actuate actuation member (714) distally, thereby opening the end effector. In addition or in the alternative, a force-feedback device may be coupled to trigger (752) to provide a resistive feedback force as the user actuates trigger (752). Such feedback may be varied according to the output from one or more sensors, such as yoke sensor (194), strain gauge (286), and/or any other sensor indicating the force being applied via actuation member (714). Further still, motor assembly (720) may be carried by a slidable member (not shown) such that a user may manually actuate actuation member (714) using trigger (752) over large distances while utilizing distal force sensitive resistor (764) and/or proximal force sensitive resistor (766) with motor (722) for finer movements. In a further version still, trigger (752) may be coupled to actuation member (714) and distal force sensitive resistor (764) and/or proximal force sensitive resistor (766) activate motor (722) to provide additional power to actuate actuation member (714). Such power assisted operation may be tuned by one or more gain knobs (not shown) on casing (702). Of course still other configurations for trigger assembly (750) will be apparent to one of ordinary skill in the art in view of the teachings herein. For instance, trigger assembly (750) may be constructed in accordance with at least some of the teachings of U.S. Pat. No. 7,770,775, entitled "Motor-Driven Surgical Cutting and Fastening Instrument with Adaptive User Feedback," issued Aug. 10, 2010, the disclosure of which is incorporated by reference herein.

V. Exemplary End Effector Having a Micro Coil

In some instances it may be useful for the user to detect whether a metallic object is near the end effector. For instance, metallic objects such as staples, pins, portions of a retractor, etc. may be undesirable to clamp onto or attempt to cut through with the end effector. Moreover, for devices that transmit electrical power through one or more components in the end effector, contact with the metallic object may cause a short circuit, thereby potentially damaging the device or compromising the surgical integrity of the surgical site. In such instances, it may be preferable to detect the presence of such objects before clamping onto the tissue and/or attempting to cut through the metallic object. Accordingly, providing a micro eddy current coil on or near the tip of an end effector may permit the user to detect such metallic objects.

FIG. 10 depicts an exemplary end effector (800) having a micro coil (810) located at a distal end of end effector (800). In the present example, micro coil (810) is located at a distal end of an upper jaw (802) of end effector (800), though it should be understood that micro coil (810) could alternatively be located at a distal end of a lower jaw (804) or anywhere else within or on end effector (800). In addition, micro coil (810) may be selectively coupleable to end effector (800) such that a user may detach micro coil (810) if micro coil (810) is not needed for the operation. In some versions, micro coil (810) is contained within a polyethylene tip to insulate micro coil (810) relative to other components of end effector (800), though this is merely optional. Indeed, in some versions micro coil (810) may be embedded in a non-conductive material of end effector (800). By way of example only, micro coil (810) may be embedded in a clamp pad, such as distal clamp pad (220) described above. Micro coil (810) of the present example is also communicatively coupled to a control unit (not shown), such as control unit (1000) described above, such that power may be supplied to micro coil (810) and the voltage running through the micro coil (810) may be monitored by the control unit. The frequencies at which micro coil (810) may operate may range from 500 Hz, inclusive, to greater than 500 kHz. For instance, micro coil (810) may operate between 700 MHz to 3 kHz. Of course other frequencies at which micro coil (810) may operate will be apparent to one of ordinary skill in the art in view of the teachings herein.

In the present example, the voltage applied to micro coil (810) produces a magnetic field extending outwardly from micro coil (810) at the distal end of end effector (800). When a metallic object is present within the magnetic field produced by micro coil (810), the magnetic field (and therefore the voltage) is disturbed. A baseline magnetic field and/or voltage reading may be tested and stored within the control unit when the surgical instrument is initially activated. Such a baseline reading takes into account the magnetic field disturbances produced by other metallic components of end effector (800). Accordingly, while end effector (800) is in use, the control unit monitors micro coil (810) to determine if any changes have occurred relative to the baseline reading. If end effector (800) and micro coil (810) encounter a metallic object, the disturbance is detected by the control unit. If a predetermined voltage deviation is encountered, control unit is configured to activate an indicator to warn the user of the presence of a metallic object. Such indicators may include a visual display (e.g. a warning light, a pop-up on a display screen, etc.), an auditory sound, a tactile feedback, etc. The control unit may also record the time, voltage deviation, and other information on an EEPROM of the control unit for later diagnostic testing of the surgical instrument and/or for logging purposes. Of course still further configurations for micro coil (810) and end effector (800) will be apparent to one of ordinary skill in the art in view of the teachings herein.

For the foregoing examples, it should be understood that the handle assemblies and/or end effectors may be reusable, autoclavable, and/or disposable. For instance, the foregoing end effectors may be disposable while the handle assemblies are reuseable and/or autoclavable. In addition, if internal power sources are used with the foregoing handle assemblies, the internal power sources may be rechargeable. For instance, the handle assemblies may be recharged using a plug in recharge, by removing and recharging the batteries, by induction, and/or by any other method as will be apparent to one of ordinary skill in the art in view of the teachings herein. Furthermore, alignment features or guides may be included to aid in the alignment and coupling of the end effectors with handle assemblies. Such guides may help prevent damage to the end effector and/or handle assembly during the assembly of the surgical instrument.

While certain configurations of exemplary surgical instruments have been described, various other ways in which surgical instruments may be configured will be apparent to those of ordinary skill in the art in view of the teachings herein. By way of example only, surgical instruments referred to herein may be constructed in accordance with at least some of the teachings of U.S. Pat. No. 6,500,176; U.S. Pat. No. 6,783,524; U.S. Pat. No. 7,416,101; U.S. Pat. No. 7,738,971; U.S. Pat. No. 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0209990, issued as U.S. Pat. No. 8,657,174 on Feb. 25, 2014; U.S. Pub. No. 2009/0043797, now abandoned; U.S. Pub. No. 2010/0069940, now U.S. Pat. No. 9,023,071, issued on May 5, 2015; and/or U.S. Provisional Application Ser. No. 61/410,603, the disclosures of which are herein incorporated by reference.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
(a) a body portion comprising at least one indicator;
(b) a transmission portion extending distally from the body portion;
(c) an end effector coupled to a distal end of the transmission portion;
(d) a control unit, wherein the at least one indicator is electrically coupled to the control unit;
(e) a toggle switch communicatively coupled to the control unit; and
(f) a plurality of sensors communicatively coupled to the control unit;
wherein at least one sensor of the plurality of sensors is operable to output a signal indicating a temperature to the control unit, wherein the temperature is associated with the surgical instrument, wherein the control unit is operable to selectively deactivate at least a portion of the end effector in response to the signal indicating the temperature from the at least one sensor,
wherein the control unit is operable to generate a control unit output signal to activate the at least one indicator in response to the signal indicating the temperature from the at least one sensor of the plurality of sensors, wherein the at least one indicator is operable to indicate a range of values in response to the control unit output signal, wherein the toggle switch is operable to manipulate the control unit output signal to the at least one indicator.

2. The surgical instrument of claim 1 further comprising a transducer, wherein the at least one sensor is mounted within the body portion, and wherein the at least one sensor of the plurality of sensors is operable to output a signal indicating a temperature of the transducer.

3. The surgical instrument of claim 2 wherein the control unit is operable to selectively deactivate the transducer.

4. The surgical instrument of claim 1 wherein the at least one sensor of the plurality of sensors is coupled to the end effector.

5. The surgical instrument of claim 1 further comprising a trigger pivotably mounted to the body portion and a trigger position sensor coupled to the trigger, wherein the trigger position sensor is communicatively coupled to the control unit, and wherein the trigger position sensor is operable to output a signal indicating a rotational position of the trigger relative to the body portion.

6. The surgical instrument of claim 1 wherein the plurality of sensors further comprises a force sensor coupled to the transmission assembly, wherein the force sensor is communicatively coupled to the control unit, and wherein the force sensor is operable to output a signal indicating a force applied to the transmission assembly.

7. The surgical instrument of claim 6 wherein the control unit is operable to activate the at least one indicator in response to the signal output from the force sensor.

8. The surgical instrument of claim 1 wherein the transmission portion further comprises an actuation member, wherein the plurality of sensors further comprises a position sensor coupled to the actuation member, wherein the position sensor is communicatively coupled to the control unit, and wherein the position sensor is operable to output a signal indicating a position of the actuation member relative to the body portion.

9. The surgical instrument of claim 8 wherein the control unit is operable to activate the at least one indicator in response to the signal output from the position sensor.

10. The surgical instrument of claim 1 wherein the end effector comprises:
 i. an upper jaw pivotably coupled to a distal end of the transmission assembly,
 ii. a clamp pad, and
 iii. a force sensor,
 wherein the force sensor is communicatively coupled to the control unit, and wherein the force sensor is operable to output a signal indicating a force applied to the upper jaw.

11. The surgical instrument of claim 10 wherein the force sensor is coupled to the clamp pad.

12. The surgical instrument of claim 10 wherein the force sensor is coupled to the upper jaw.

13. The surgical instrument of claim 10 wherein the force sensor comprises a force sensitive resistor.

14. The surgical instrument of claim 1 wherein the end effector comprises a micro coil.

15. The surgical instrument of claim 14 wherein the micro coil is coupled to the control unit, wherein the control unit is operable to apply a voltage to the micro coil, and wherein the control unit is further operable to monitor the voltage applied to the micro coil.

16. A surgical instrument comprising:
(a) a body portion comprising:
 (i) at least one indicator, and
 (ii) a control unit communicatively coupled with the at least one indicator;
(b) a transmission portion extending distally from the body portion;
(c) an end effector coupled to a distal end of the transmission portion;
(d) a toggle switch communicatively coupled to the control unit; and
(e) a plurality of sensors communicatively coupled to the control unit;
wherein the control unit is operable to selectively deactivate at least a portion of the end effector in response to a signal from a sensor of the plurality of sensors,
wherein the at least one indicator is electrically coupled to the control unit,
wherein the at least one indicator is operable receive a signal from the control unit to indicate a corresponding magnitude relative to the signal supplied by the sensor of the plurality of sensors,
wherein the toggle switch is operable to manipulate the signal received by the at least one indicator.

17. A surgical instrument comprising:
(a) a body portion comprising at least one indicator;
(b) a transmission portion extending distally from the body portion;
(c) an end effector coupled to a distal end of the transmission portion;
(d) a control unit;
(e) a toggle switch communicatively coupled to the control unit; and
(f) a plurality of sensors communicatively coupled to the control unit;
wherein the control unit is operable to selectively deactivate at least a portion of the end effector in response to a signal from at least one sensor of the plurality of sensors,
wherein the at least one indicator is electrically coupled to the control unit,
wherein the control unit is operable to activate the at least one indicator with a control unit output signal formed from the control unit receiving the signal from the at least one sensor of the plurality of sensors,
wherein the at least one indicator is operable to indicate a range of values in response to the control unit output signal,
wherein the toggle switch is operable to manipulate the control unit output signal.

18. The surgical instrument of claim 1 further comprising a trigger pivotably mounted to the body portion, wherein the transmission portion further comprises a shaft, wherein the plurality of sensors comprises a force measuring sensor coupled to the trigger and the shaft, wherein the force measuring sensor is operable to transmit a signal to the control unit indicating a force applied from the trigger to the shaft.

* * * * *